(12) United States Patent
Soeda et al.

(10) Patent No.: US 9,456,844 B2
(45) Date of Patent: Oct. 4, 2016

(54) ATHERECTOMY DEVICE

(71) Applicant: NIPRO CORPORATION, Osaka (JP)

(72) Inventors: Nobuyuki Soeda, Fukushima (JP); Katsuya Miyagawa, Osaka (JP); Yuuki Nishimura, Osaka (JP); Misa Kakinoki, Osaka (JP)

(73) Assignee: NIPRO CORPORATION, Osaka (JP)

( * ) Notice: Subject to any disclaimer, the term of this patent is extended or adjusted under 35 U.S.C. 154(b) by 176 days.

(21) Appl. No.: 14/360,722

(22) PCT Filed: Oct. 30, 2012

(86) PCT No.: PCT/JP2012/078052
§ 371 (c)(1),
(2) Date: May 27, 2014

(87) PCT Pub. No.: WO2013/080730
PCT Pub. Date: Jun. 6, 2013

(65) Prior Publication Data
US 2014/0336684 A1    Nov. 13, 2014

(30) Foreign Application Priority Data
Nov. 28, 2011    (JP) .................................. 2011-258407

(51) Int. Cl.
*A61B 17/3207*    (2006.01)
*A61B 17/00*    (2006.01)
*A61B 17/22*    (2006.01)

(52) U.S. Cl.
CPC .................. *A61B 17/320758* (2013.01); *A61B 17/320783* (2013.01); *A61B 2017/00734* (2013.01); *A61B 2017/22071* (2013.01); *A61B 2017/320791* (2013.01)

(58) Field of Classification Search
CPC .................. Y02T 10/7005; A61B 17/320758
USPC .......................................... 318/139, 34, 558
See application file for complete search history.

(56) References Cited

U.S. PATENT DOCUMENTS 5,135,483 A * 8/1992 Wagner .......... A61B 17/320758
600/564
5,261,877 A * 11/1993 Fine ................ A61B 17/320758
604/22

(Continued)

FOREIGN PATENT DOCUMENTS

| EP | 0 163 502 | 5/1985 |
| JP | 61-56639 | 3/1986 |
| JP | 62-266046 | 11/1987 |
| JP | 2-223395 | 9/1990 |

(Continued)

OTHER PUBLICATIONS

Supplementary European Search Report dated Mar. 31, 2015 for PCT/JP2012/078052.

*Primary Examiner* — David S Luo
(74) *Attorney, Agent, or Firm* — Jordan and Koda PLLC

(57) ABSTRACT

An atherectomy device has a drive circuit which rotates a direct-current motor. The drive circuit has a three-terminal regulator having an ADJ terminal. A partial pressure resistor is connected between the ADJ terminal and an output terminal of the three-terminal regulator. Moreover, one end of six variable resistors whose resistances are set to be different from each other is connected to the ADJ terminal. The other end of the six variable resistors is selectively connected to the negative electrode of a battery by a change-over switch which is a rotary switch having six contacts. When the variable resistors are switched by the change-over switch, the output current of the three-terminal regulator becomes large. Thus, the rotation speed of a cutter which is rotated by the direct-current motor becomes high.

9 Claims, 15 Drawing Sheets

(56) References Cited

U.S. PATENT DOCUMENTS

| | | |
|---|---|---|
| 7,037,316 B2 * | 5/2006 | McGuckin, Jr. ....... A61B 17/22 606/113 |
| 7,883,476 B2 | 2/2011 | Miller et al. |
| 8,109,886 B2 | 2/2012 | Miller et al. |
| 8,764,679 B2 | 7/2014 | Miller et al. |
| 8,986,222 B2 | 3/2015 | Miller et al. |
| 2005/0113715 A1 | 5/2005 | Schwindt et al. |
| 2012/0059276 A1 | 3/2012 | Miller et al. |

FOREIGN PATENT DOCUMENTS

| | | |
|---|---|---|
| JP | 6-319745 | 11/1994 |
| JP | 11-347040 | 12/1999 |
| JP | 2000-210299 | 8/2000 |
| JP | 2004-066640 | 3/2004 |
| JP | 2007-313332 | 12/2007 |
| JP | 2010-213801 | 9/2010 |
| WO | WO-99/52454 | 10/1999 |
| WO | WO-02/069808 | 9/2002 |

* cited by examiner (A)

(B)

ATHERECTOMY DEVICE

TECHNICAL FIELD

The present invention relates to an atherectomy device for excising an atheroma generated in a blood vessel.

BACKGROUND OF THE INVENTION

Heretofore, an atherectomy device which excises an atheroma generated in a blood vessel is known (for example, refer to Patent Literature 1). A rotational atherectomy device described in Patent Literature 1 has a controller (atherectomy device) having a motor and a flexible tubular body (catheter) which is extended from the controller and is inserted into a blood vessel. To the distal end portion of the flexible tubular body, a cutter which is rotated by the motor is provided. An atheroma is scraped and excised by the rotated cutter.

Moreover, in the rotational atherectomy device described in Patent Literature 1, a battery and a power supply circuit (substrate) are disposed in the controller. The power supply circuit has a switching regulator. The power supply circuit inputs a constant voltage to the motor.

CITATION LIST

PTL 1: Japanese Unexamined Patent Application Publication No. 11-347040

In the excision of an atheroma for which the atherectomy device is used, the flexible tubular body is inserted into a blood vessel. The blood flow is inhibited by the flexible tubular body, and then it is required to shorten the time required for an operation of excising the atheroma to reduce the burden to a patient.

In order to shorten the time required for the atheroma excision operation, it is supposed to make the number of rotations of the motor changeable to facilitate the atheroma excision operation or facilitate the handling of the atherectomy device.

However, the number of rotations of the motor cannot be changed in the power supply circuit described in Patent Literature 1. Moreover, since the battery and the power supply circuit are disposed in the controller, there is no cable and the device is easy to handle but the size of the controller increases corresponding to the battery and the power supply circuit (substrate) and the ease of handling has decreased to half.

In order to reduce the size of the controller, it is proposed to directly connect a battery and a direct-current motor through a power switch. Thus, a voltage higher than the rated voltage of the motor is required to be input into the motor in order to obtain sufficient torque which allows excision of an atheroma, which poses problems of a failure of the motor, an increase in the heat generation amount in the motor, and an increase in the exhaustion rate (a reduction in the available time) of the battery.

SUMMARY OF THE INVENTION

The present invention has been made in view of the above-described circumstances. It is an object of the present invention to provide a measure capable of shortening the time required for excision of an atheroma.

SOLUTION TO PROBLEM (1) To an atherectomy device of the present invention, a catheter having a tubular body having an opening in the side wall and a cutter which is provided movably in the axial direction in the tubular body is connected. The atherectomy device of the present invention has a direct-current motor which rotates the cutter, a three-terminal regulator which has an input terminal, an output terminal, and an ADJ terminal and in which one of a pair of input terminals of the direct-current motor is connected to the output terminal, a partial pressure resistor connected between the output terminal and the ADJ terminal of the three-terminal regulator, a resistor group having a plurality of fixed resistors or a plurality of variable resistors whose resistances are different from each other and one end of which is connected to the ADJ terminal, and a change-over switch which selectively connects one of the other ends of the plurality of fixed resistors or the variable resistors of the resistor group to the other input terminal of the direct-current motor.

The tubular body is inserted into a blood vessel. An atheroma adhering to the inner wall of the blood vessel is made to enter the tubular body from the opening provided in the side wall of the tubular body. In this state, the cutter which is rotated by the direct-current motor is moved in the axial direction in the tubular body to be pressed against the atheroma in the opening. Thus, the atheroma is scraped, and then the scraped atheroma is collected in the tubular body. The direct-current motor which rotates the cutter is driven by a direct current supplied from the three-terminal regulator. For the three-terminal regulator, one having an input terminal, an output terminal, and an ADJ terminal is used. In the three-terminal regulator having the ADJ terminal, the current value of the direct current to be output is determined based on the resistance ratio of the partial pressure resistor to be connected between the ADJ terminal and the output terminal and the partial pressure resistor to be connected between the ADJ terminal and a constant voltage, such as ground. A user operates the change-over switch to switch the partial pressure resistor to be connected between the ADJ terminal and the constant voltage to another resistor from one of the plurality of resistors (fixed resistors or variable resistors) whose resistances are different from each other. Thus, the current value of the direct current output by the three-terminal regulator changes, the rotation speed (unloaded state) of the direct-current motor changes, and then the rotation speed of the cutter changes. The user increases the rotation speed of the cutter according to the hardness and the type of the atheroma to excise the atheroma.

(2) The resistor group may be one having a plurality of potentiometers.

The rotation speed of the cutter is determined based on the resistance of the resistor connected between the ADJ terminal and the constant voltage. By the use of a potentiometer (variable resistor) for the resistor, the rotation speed of the cutter can be easily adjusted according to a specification before delivery and the like. Moreover, by the use of the potentiometer, a user can be prevented from accidentally changing the resistance. Moreover, by the use of the potentiometer, an increase in an error of the resistance due to changes with time can be suppressed as compared with a case of using a mechanical variable resistor in which a movable piece slides on a resistor.

(3) The atherectomy device of the present invention may further has a setting unit which inputs a pulse into the potentiometers to set the resistance on condition that a current is supplied to the three-terminal regulator. Since the resistance of the potentiometer is set whenever the power supply is turned ON, a state where the resistance of the potentiometer is erroneously set is not maintained.

(4) The atherectomy device of the present invention may further have a first casing provided with the direct-current motor and having a grip, a second casing provided with a socket to which a battery which supplies a direct current to the three-terminal regulator is attached, the three-terminal regulator, the resistor group, and the change-over switch, and a cable which electrically connects the output terminal of the three-terminal regulator and the input terminal of the direct-current motor.

A user grasps the grip of the first casing to hold the first casing in the hand, and inserts the tubular body into a blood vessel. Since the battery is attached to the second casing, the weight of the first casing held in the hand can be reduced, which facilitates the handling of the atherectomy device. Moreover, since the battery is not attached to the first casing, a large capacity battery or a large number of batteries can be used and the period of time while the atherectomy device can be continuously used can be prolonged. Moreover, since the change-over switch is provided in the second casing, the first casing does not accidentally move when operating the change-over switch.

(5) The atherectomy device of the present invention may further have a first casing provided with the direct-current motor, the resistor group, and the change-over switch and having a grip, a second casing provided with a socket to which a battery is attached, and a cable which electrically connects the battery attached to the socket and an input terminal of the three-terminal regulator.

A user grasps the grip of the first casing to hold the first casing in the hand, and inserts the tubular body into a blood vessel. Since the battery is attached to the second casing, the weight of the first casing hold in the hand can be reduced, which facilitates the handling of the atherectomy device. Moreover, since the battery is not attached to the first casing, a large capacity battery or a large number of batteries can be used and the period of time while the atherectomy device can be continuously used can be prolonged. Moreover, since the change-over switch is provided in the first casing held in the hand, the user can change the rotation speed of the cutter unless the user reaches for the second casing.

(6) The atherectomy device of the present invention may further have a first casing provided with a first casing provided with a socket to which a battery which supplies a direct current to the three-terminal regulator is attached, the direct-current motor, the three-terminal regulator, the resistor group, and the change-over switch and having a grip.

When the socket and the change-over switch are disposed outside the first casing, a cable is required to be connected to the first casing. By providing the socket, the direct-current motor, the three-terminal regulator, the resistor group, and the change-over switch in the first casing, a necessity of connecting a cable to the first casing is eliminated and a user can freely move the first casing held in the hand.

(7) The change-over switch may be a rotary switch.

(8) The atherectomy device of the present invention further has a socket to which a battery is attached and a detection circuit which detects the voltage of the battery, in which the detection circuit has a partial pressure resistor circuit which divides the voltage of the battery to output the divided voltage, a switching element which is turned ON by the output voltage of the partial pressure resistor circuit, and a notification portion which performs notification when the switching element is turned ON, in which one of the partial pressure resistors constituting the partial pressure resistor circuit may be a variable resistor.

When the voltage of the battery is equal to or higher than the predetermined voltage, the switching element is turned ON, and then the notification portion performs notification. When the voltage of the battery is less than the predetermined voltage, the switching element is not turned ON, and thus the notification portion does not perform notification. A user can confirm that the voltage of the battery is sufficiently high based on the notification performed by the notification portion. The predetermined voltage is determined based on the resistance ratio of the partial pressure resistor circuit. The resistance ratio of the partial pressure resistor circuit can be changed based on the resistances of the variable resistors. Therefore, the predetermined voltage can be freely adjusted according to a specification before delivery and the like.

(9) To the atherectomy device of the present invention, a catheter having a tubular body having an opening in the side wall and a cutter which is provided movably in the axial direction in the tubular body is connected. The atherectomy device of the present invention has a bodycasing which has a connection portion to which the catheter is connected and a grip and in which a socket to which a battery is attached is provided, a substrate in which a three-terminal regulator having an input terminal, an output terminal, and an ADJ terminal is mounted and which is disposed in the bodycasing, a power switch electrically connected between the battery and an input terminal of the three-terminal regulator, a direct-current motor which is disposed in the bodycasing, which is connected to the output terminal of the three-terminal regulator, and which rotationally drives a cutter of the catheter, and a partial pressure circuit provided between the output terminal and the ADJ terminal of the three-terminal regulator in the substrate.

By the three-terminal regulator and the partial pressure circuit, the rated voltage can always be input into the direct-current motor. Therefore, a failure of the battery can be suppressed, exhaustion of the battery can be suppressed, and a driving force which allows excision of an atheroma can be obtained from the direct-current motor.

Moreover, since the battery, the power switch, the direct-current motor, and the substrate are disposed in the bodycasing, a necessity of connecting a cable to the bodycasing is eliminated, and a user can freely move the bodycasing held in the hand. Moreover, since the three-terminal regulator is used, the size of the device can be reduced as compared with a case of using a switching regulator. There is not necessity of connecting a cable and the size can be reduced, and therefore the handling of the device is facilitated.

(10) A light emitting element connected in parallel to the direct-current motor may be provided. It can be easily confirmed whether the direct-current motor operates based on lighting on or off of the light emitting element. Moreover, a deficient portion is easily specified by the light emitting element.

According to the present invention, due to the fact that the resistor group and the change-over switch are provided, the rotation speed of the cutter can be made high according to the hardness of an atheroma, so that the atheroma can be quickly excised. Moreover, the rotation speed of the cutter can be instantly made high by the change-over switch. As a result, the time required for the excision of the atheroma can be shortened. Moreover, due to the fact that the three-terminal regulator is used in an integral type in which the battery is disposed in the bodycasing, a failure of the battery can be suppressed, exhaustion of a battery can be suppressed, a driving force which allows the atheroma excision can be obtained from the direct-current motor, and the size of the device can be reduced, so that the time required for the atheroma excision can be shortened.

DESCRIPTION OF THE PREFERRED EMBODIMENTS

Hereinafter, preferable embodiments of the present invention are described. A first embodiment and a second embodiment merely describe one embodiment of the present invention and it is a matter of course that the embodiments can be altered in a range where the gist of the present invention is not altered.

Figure 1:
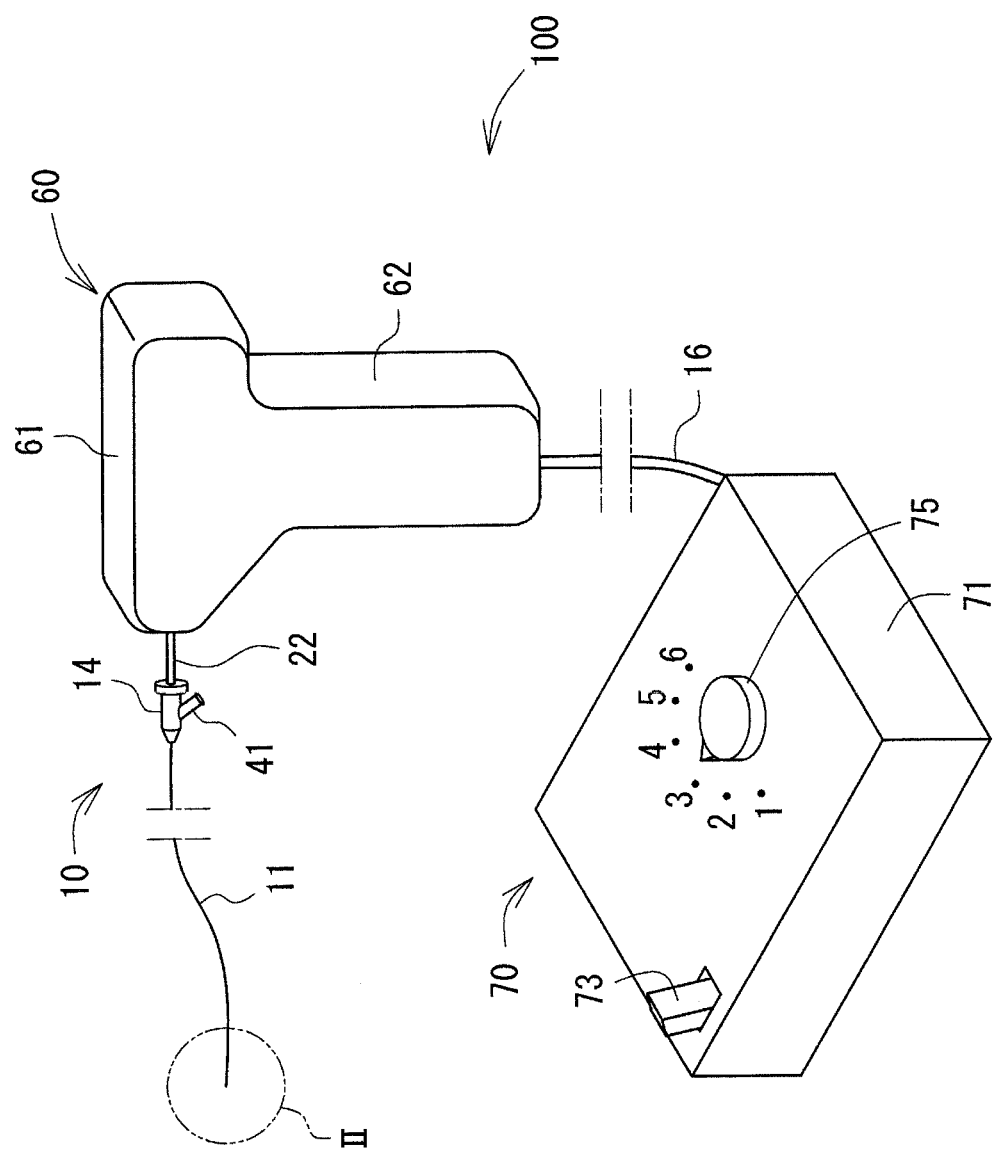
FIG. 1 is a perspective view of the appearance of an atherectomy device of a first embodiment.

An atherectomy device 100 illustrated in FIG. 1 is used as a medical implement for excising an atheroma 51 (FIG. 3) generated in a blood vessel 50. The atherectomy device 100 has a power supply body 70 to be laid on a desk or a stand and an operation body 60 electrically connected to the power supply body 70 by a cable 16 and is held in the hand for use. To the operation body 60, a catheter 10 is connected.

Figure 2:
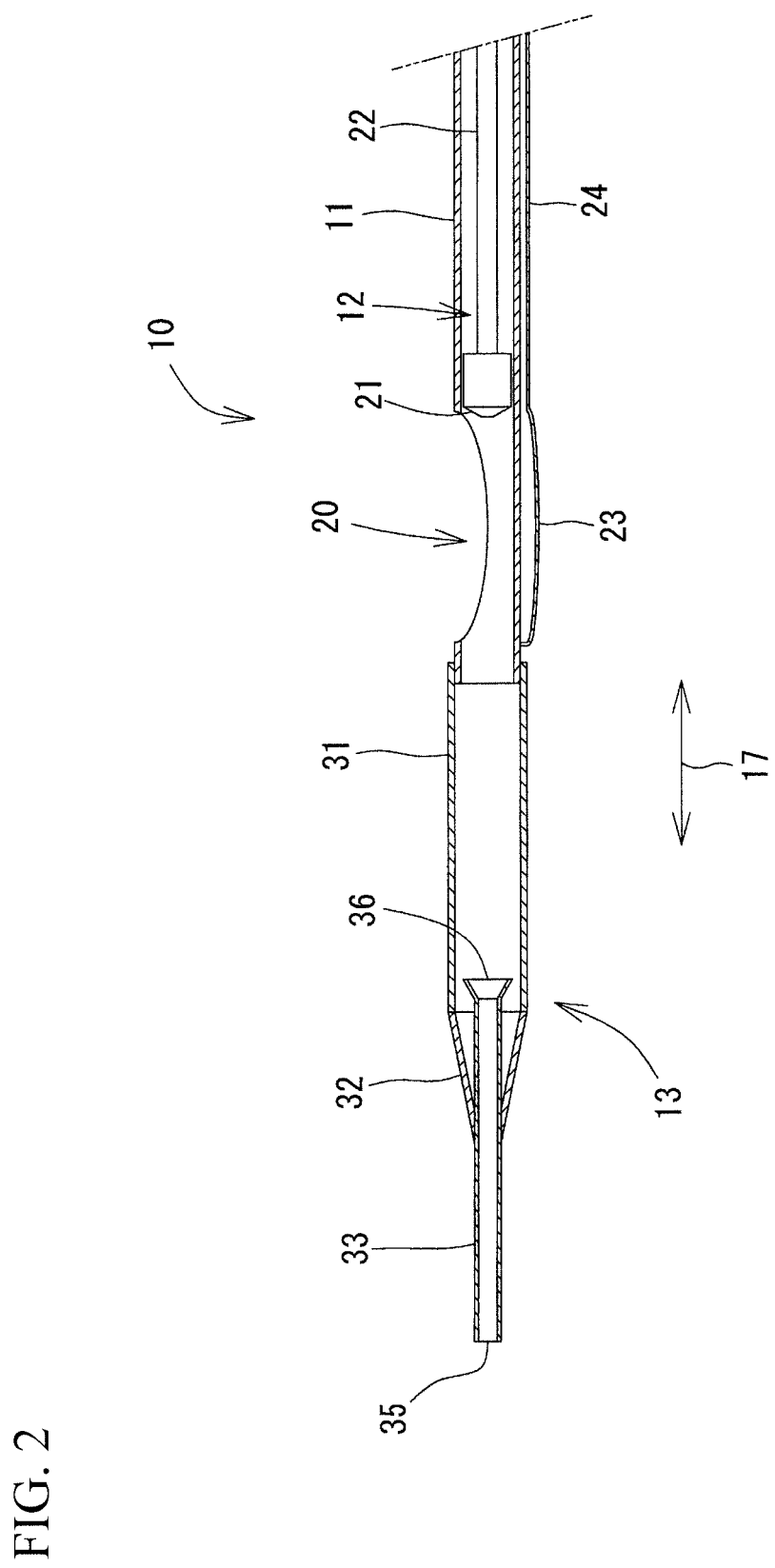
FIG. 2 is a cross sectional view of a catheter which passes through the axis line of a shaft in II of FIG. 1.

As illustrated in FIG. 2, the catheter 10 has a shaft 11, a cutter 12 provided in the shaft 11, a distal end portion 13 constituting the distal end of the shaft 11, and a proximal end portion 14 (FIG. 1) connected to the proximal end of the shaft 11.

Figure 3:
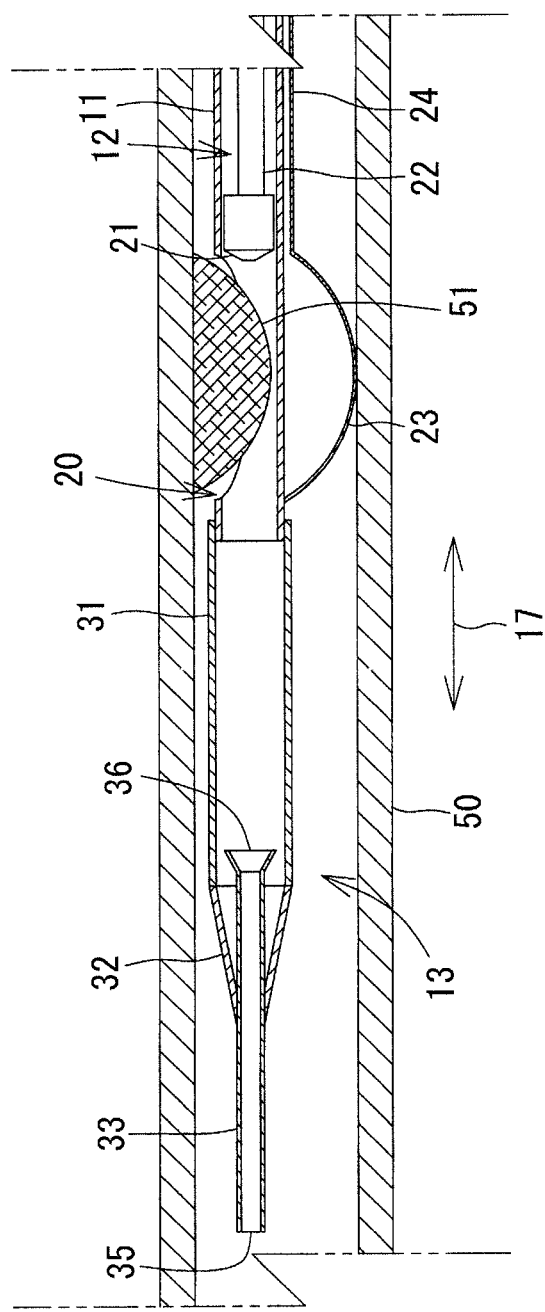
FIG. 3 is a schematic view illustrating a state where a balloon is expanded in a blood vessel.

As illustrated in FIG. 2, the shaft 11 is a tube capable of containing the cutter 12 inside. The shaft 11 is constituted by a stainless steel cylindrical tube or a synthetic resin cylindrical tube, for example, and has flexibility which allows the shaft 11 to elastically curve according to the curved shape of a blood vessel 50 (FIG. 3). The distal end and the proximal end of the shaft 11 each open. The outer diameter of the shaft 11 is set according to the inner diameter of a blood vessel 50 into which the shaft 11 is to be inserted, for example, the coronary artery. The inner diameter of the shaft 11 is set according to the outer diameter of the cutter 12. The outer diameter and the inner diameter of the shaft 11 are almost equal over the axial direction 17 of the shaft 11. The length in the axial direction 17 of the shaft 11 is set considering the length from the catheter insertion portion to the affected portion, such as the human limbs.

As illustrated in FIG. 2, in the side wall of the shaft 11, an opening 20 is formed near the distal end portion 13. The opening 20 is formed by partially cutting the side wall of the shaft 11. The shape and the size of the opening 20 are set considering the shape and the size of the atheroma 51 (FIG. 3) which may be formed in the affected portion. The shaft 11 is equivalent to the tubular body.

As illustrated in FIG. 2, in the internal space of the shaft 11, the cutter 12 is provided near the opening 20. The cutter 12 has a cutting portion 21 and a shaft 22. The cutting portion 21 has almost a cylindrical shape and the outer diameter is a little smaller than the inner diameter of the shaft 11. On the distal end side of the cutting portion 21, a plurality of edges are formed in such a manner as to radially extend from the center. Although not illustrated in FIG. 2, a through-hole is formed in the center of the cutting portion 21 along an axial direction 17.

The shaft 22 is extended from the proximal end of the cutting portion 21 to the outside of the proximal end portion 14 (FIG. 1). The shaft 22 is a narrow and long tube and the internal space communicates with the through-hole of the cutting portion 21. The internal space of the shaft 22 and the through-hole of the cutting portion 21 are those for passing a guide wire (not illustrated). The shaft 22 is rotated by a direct-current motor M (FIG. 5) provided in the operation body 60. When the shaft 22 is rotated, the cutting portion 21 rotates. Moreover, when the shaft 22 is moved in the axial direction 17, the cutting portion 21 moves in the axial direction 17 in the internal space of the shaft 11.

As illustrated in FIG. 2, a balloon 23 is provided at a position opposite to the opening 20 with respect to the shaft 11. The balloon 23 can expand outward from the side wall of the shaft 11 and is folded and adheres to the side wall of the shaft 11 until the catheter 10 is inserted into the blood vessel 50 (FIG. 3). The material of the balloon 23 is preferably a material having biocompatibility and specifically includes polyurethane, polyethylene, polyester, polypropylene, polyamide, a polyamide elastomer, polytetrafluoroethylene, polyvinylidene fluoride, and the like.

As illustrated in FIG. 2, the proximal end side of the balloon 11 is connected to an outer tube 24 provided along the side wall of the shaft 11. The internal space of the outer tube 24 communicates with the internal space of the balloon 23. The outer tube 24 is extended to the proximal end portion 14 (FIG. 1). The internal space of the outer tube 24 is continuous to the internal space of a port 41 of the proximal end portion 14. When liquid, such as physiological saline, injected from the port 41 of the proximal end portion 14 is made to flow into the balloon 23, the balloon 23 expands in the blood vessel 50 (FIG. 3). The outer tube 24 is a molded body of a soft plastic which can elastically deform, such as polyamide, a polyamide elastomer, and polyetheramide.

As illustrated in FIG. 2, the distal end portion 13 is connected to the distal end of the shaft 11. The distal end portion 13 has a blade tube 31, a reduced diameter portion 32, and a distal end tip 33. The blade tube 31 is a cylindrical tube whose both sides open. The blade tube 31 is one in which a soft plastic which can elastically deform, such as polyamide, a polyamide elastomer, and polyetheramide, is reinforced by a core material which is not illustrated. The blade tube 31 is connected to the distal end of the shaft 11 and the internal space communicates with the internal space of the shaft 11. The reduced diameter portion 32 is a cylindrical tube whose both sides open and whose outer diameter decreases in a tapered shape. The reduced diameter portion 32 is connected to the distal end of the blade tube 31 and the internal space is continuous to the internal space of the blade tube 31

The reduced diameter portion 32 contains a soft plastic which can elastically deform, such as polyamide, an polyamide elastomer, and polyetheramide. The inner diameter on the proximal end side of the reduced diameter portion 32 is almost equal to the outer diameter of the distal end of the blade tube 31. The reduced diameter portion 32 is fitted into the distal end of the blade tube 31 from the outside and thermally fused. The inner diameter on the distal end side of the reduced diameter portion 32 is almost equal to the outer diameter of the central portion of the distal end tip 33.

The distal end tip 33 is a cylindrical tube whose both sides open and whose outer diameter increases in a tapered shape on the side of a proximal end 36. The distal end tip 33 is connected to the distal end of the reduced diameter portion 32 and the internal space is continuous to the internal space of the reduced diameter portion 32. A distal end 35 of the distal end tip 33 is projected outward in the axial direction 17 from the distal end of the reduced diameter portion 32. The proximal end 36 side of the distal end tip 33 extends the internal space of the reduced diameter portion 32 in the axial direction 17 and the proximal end 36 reaches the internal space of a blade tube 31.

As illustrated in FIG. 1, on the proximal end of the shaft 11, a proximal end portion 14 is provided. The proximal end portion 14 is a cylindrical member having an internal space continuous to the internal space of the shaft 11. The proximal end portion 14 is a molded body of resin, such as polypropylene and ABS. The proximal end portion 14 may serve as a handle in an operation of inserting or removing the shaft 11 into/from the blood vessel 50 (FIG. 3).

The proximal end portion 14 is provided with a port 41 extended in a direction crossing to the axial direction 17 (FIG. 2). When another device, such as a syringe, is connected to the port 41, fluid, such as physiological saline, which is made to flow into/out of another device flows into/out of the outer tube 24 (FIG. 2) from the proximal end portion 14. The proximal end portion 14 may be provided with another port continuous to the internal space of the shaft 11 (FIG. 2). Such a port is used for the purpose of, for example, collecting pieces 12 of an excised atheroma 51 and the like.

Figure 5:
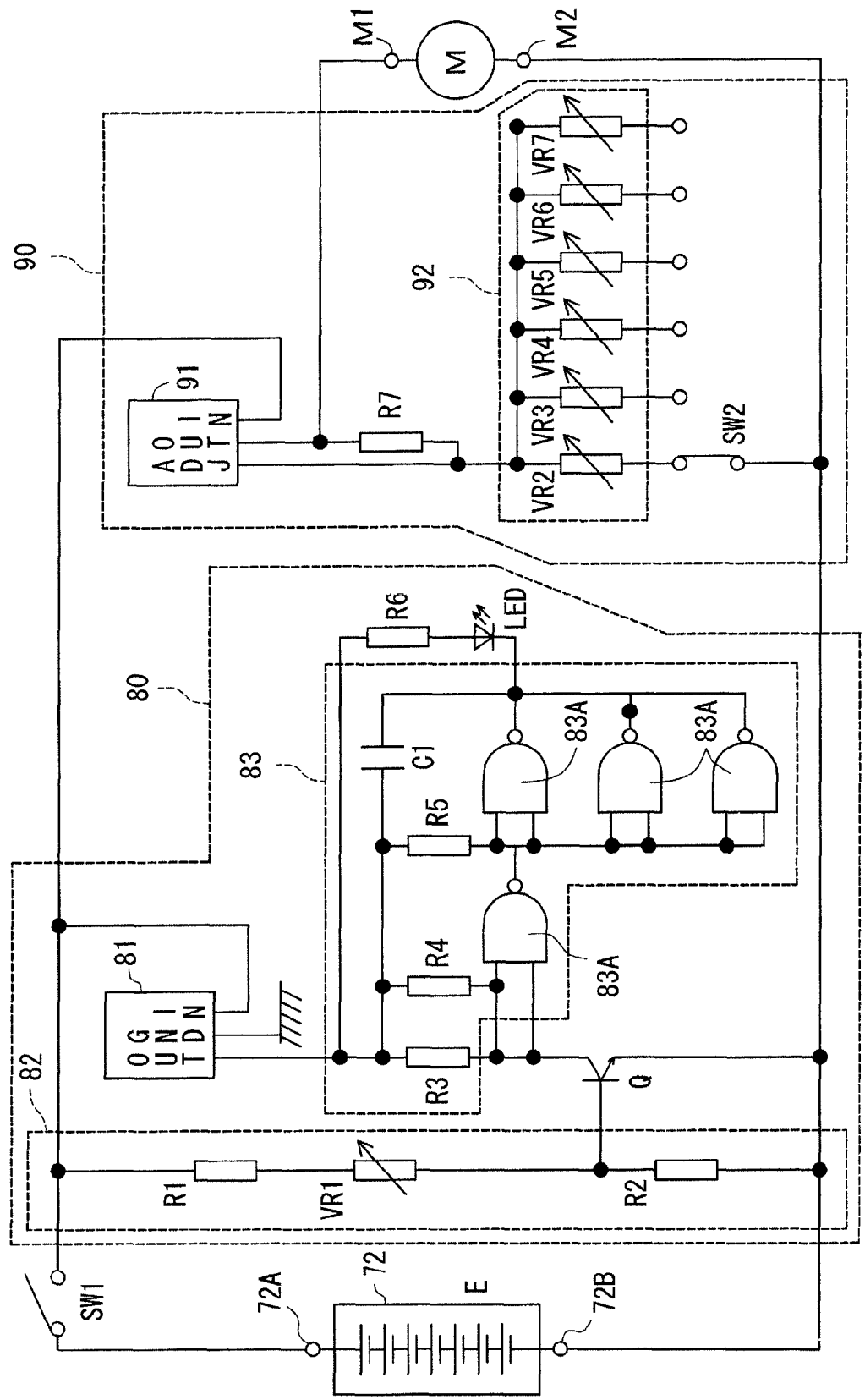
FIG. 5 is a circuit diagram of the atherectomy device.

As illustrated in FIG. 1, the operation body 60 has a casing 61 provided with a grip 62 which a user grasps. The casing 61 is equivalent to the first casing. In the casing 61, a direct-current motor M (FIG. 5) which rotates the shaft 22 (FIG. 2) of the cutter 12 is disposed. As illustrated in FIG. 5, one input terminal M1 of the direct-current motor M is connected to an output terminal (OUT) of a three-terminal regulator 91 described later through a cable 16 (FIG. 1). The other input terminal M2 is electrically connected to a negative electrode of a battery E through a negative electrode terminal 72B of a socket 72.

A power supply body 70 illustrated in FIG. 1 is laid on a desk or a stand for use. The power supply body 70 has a casing 71. The casing 71 is equivalent to the second casing. In the casing 71, a power switch SW1, the socket 72 to which the battery is attached, and various electronic components realizing a detection circuit 80 and a drive circuit 90 illustrated in FIG. 5 are provided. The detection circuit 80 is a circuit which detects a voltage reduction of the battery. The drive circuit 90 is a circuit which drives the direct-current motor M. In the following description, "connected" means "electrically connected by a lead wire and a substrate pattern".

The socket 72 illustrated in FIG. 5 is provided in such a manner that a plurality of batteries can be attached thereto. The plurality of batteries are connected in series in the socket 72. Hereinafter, a description is given referring to the plurality of batteries collectively as the battery E. The socket 72 has a positive electrode terminal 72A which abuts to the positive electrode of the battery E and a negative electrode terminal 72B which abuts to the negative electrode of the battery.

For the power switch SW1, a mechanical power switch having a movable section which is moved by being operated by a user and two terminals connected or opened by the movable section. One of the terminals of the power switch SW1 is connected to the positive electrode terminal 72A of the socket 72. The other terminal of the power switch SW1 is connected to a partial pressure resistor circuit 82 and three-terminal regulators 81 and 91 described later. As illustrated in FIG. 1, an operation lever 73 which moves the movable section is exposed to the outside of the casing 71 of the power supply body 70. When the operation lever 73 is operated, and then the power switch SW1 is turned ON, a direct current is supplied to the three-terminal regulator 91, so that the direct-current motor M is driven.

As illustrated in FIG. 5, the detection circuit 80 has the three-terminal regulator 81, a voltage regulation resistor R6, a light emitting diode LED, the partial pressure resistor circuit 82, a switching element Q containing a NPN transistor, and a protective circuit 83. The light emitting diode LED is equivalent to the notification portion.

The three-terminal regulator 81 has an input terminal (IN), an output terminal (OUT), and a GND terminal. The input terminal of the three-terminal regulator 81 is connected to a terminal, which is not connected to the battery E, of the power switch SW1. When the power switch SW1 is turned ON, a direct current is supplied to the three-terminal regulator 81 from the battery E. The GND terminal of the three-terminal regulator 81 is grounded.

To the output terminal of the three-terminal regulator 81, one end of the voltage regulation resistor R6 is connected. The other end of the voltage regulation resistor R6 is connected to an anode of the light emitting diode LED. The direct current output from the three-terminal regulator 81 flows into the light emitting diode LED through the voltage regulation resistor R6. The current value of the direct current which flows into the light emitting diode LED is adjusted based on the resistance of the voltage regulation resistor R6.

A cathode of the light emitting diode LED is connected to a collector of the switching element Q through the protective circuit 83. The collector of the switching element Q is connected to the output terminal of the three-terminal regulator 81 through a resistor R3 of the protective circuit 83. An emitter of the switching element Q is connected to the negative electrode terminal 72B of the socket 72.

When a drive voltage is applied to a base of the switching element Q, and then the switching element Q is turned ON, a direct current flows into the light emitting diode LED, and then the light emitting diode LED is lighted on. When the switching element Q is turned OFF, a circuit which passes a direct current to the light emitting diode LED is partially opened, and then the light emitting diode LED is lighted off. The protective circuit 83 is a circuit which protects the light emitting diode LED and is constituted by four NAND circuits 83A, three resistors R3 to R5, and a capacitor C1. Since a circuit having an existing configuration can be used as the protective circuit 83, a detailed description of the protective circuit 83 is omitted.

The switching element Q is turned ON/OFF by the partial pressure resistor circuit 82. The partial pressure resistor circuit 82 has a partial pressure resistor R1 one end of which is connected to a terminal, which is not connected to the battery E, of the power switch SW1, a variable resistor VR1 one end of which is connected to the other end of the partial pressure resistor R1, and a partial pressure resistor R2 connected to the other end of variable resistor VR1. The base of the switching element Q is connected to the connection end of the variable resistor VR1 and the partial pressure resistor R2.

When the power switch SW1 is turned ON, the voltage of the battery E is divided into the partial pressure resistor R1 and the variable resistor VR1 and the partial pressure resistor R2 to be output. The partial pressure ratio is given by (Resistance of the combined resistance of the partial pressure resistor R1 and variable resistor VR1):(Resistance of the partial pressure resistor R2).

When the voltage of the battery E is sufficiently high and the voltage output form the partial pressure resistor circuit 82 is higher than the drive voltage (threshold voltage) of the switching element Q, the switching element Q is turned ON. Thus, the light emitting diode LED is lighted on. When the voltage of the battery E decreases, and the voltage output from the partial pressure resistor circuit 82 is lower than the drive voltage of the switching element Q, the switching element Q is not turned ON. Then, the light emitting diode LED is not turned ON. Therefore, it can be judged whether the voltage of the battery E is equal to or higher than the predetermined voltage based on whether the light emitting diode LED is lighted on when the power switch SW1 is turned ON. Or, it can be judged that the voltage of the battery E became is less than the predetermined voltage based on the fact that the light emitting diode LED is lighted off during the use of the atherectomy device 100.

The predetermined voltage is determined based on the partial pressure ratio of the partial pressure resistor circuit 82. The partial pressure ratio can be adjusted by the variable resistor VR1. The resistance of the variable resistor VR1 is adjusted according to a specification before delivery and the like. For example, the resistance of the variable resistor VR1 is adjusted in such a manner that the light emitting diode LED is not lighted on when the remaining period of time while the direct-current motor M can be driven is 10 minutes, 20 minutes, or 30 minutes.

The drive circuit 90 is a circuit which drives the direct-current motor M. The drive circuit 90 has the three-terminal regulator 91, a partial pressure resistor R7, a resistor group 92 having variable resistors VR2 to VR7, and a change-over switch SW2. The change-over switch SW2 is one for selecting one variable resistor out of the six variable resistors VR2 to VR7, and connecting the resistor to the three-terminal regulator 91 to thereby change the rotation speed of the cutter 12. Hereinafter, a detailed description is given.

The three-terminal regulator 91 has an input terminal (IN), an output terminal (OUT), and an ADJ terminal. The input terminal of the three-terminal regulator 91 is connected to the terminal, which is not connected to the battery E, of the power switch SW1. When the power switch SW1 is turned ON, a direct current is supplied to the three-terminal regulator 91 from the battery E.

The partial pressure resistor R7 is connected between the output terminal and the ADJ terminal of the three-terminal regulator 91. The ADJ terminal is connected to one end of each of the variable resistors VR2 to VR7. The other end of each of the variable resistors VR2 to VR7 is connected to or disconnected from the negative electrode terminal 72B of the socket 72 or opened by the change-over switch SW2. Therefore, the three-terminal regulator 91 outputs a direct current of the current value according to the partial pressure ratio between the resistance of the variable resistor selected by the change-over switch SW2 and the partial pressure resistor R7.

The change-over switch SW2 is a two-circuit-six-contact rotary switch in which a common terminal is connected to the negative electrode terminal 72B of the socket 72. The six-contact rotary switch is used in order that the six variable resistors VR2 to VR7 are used. The two-circuit rotary switch is used in order that two potentiometers 93 (FIG. 6) connected in parallel are used as each of the variable resistors VR2 to VR7. The two potentiometers 93 are used as each of the variable resistors VR2 to VR7 in order to adjust the range of the resistance of the variable resistors. In detail, two potentiometer 93 whose maximum set resistance is 10 kΩ are connected in parallel to be used as the variable resistors VR2 to VR7 whose maximum preset value is 5 kΩ. The six variable resistors VR2 to VR7 are constituted by the 12 potentiometers 93.

The contact of the change-over switch SW2 is switched by a knob 75 illustrated in FIG. 1. When the knob 75 is turned to "1", "2", "3", "4", "5", and "6" illustrated FIG. 1, each of the variable resistors VR2, VR3, VR4, VR5, VR6, and VR7 is connected to the negative electrode terminal 72B of the socket 72.

Figure 6:
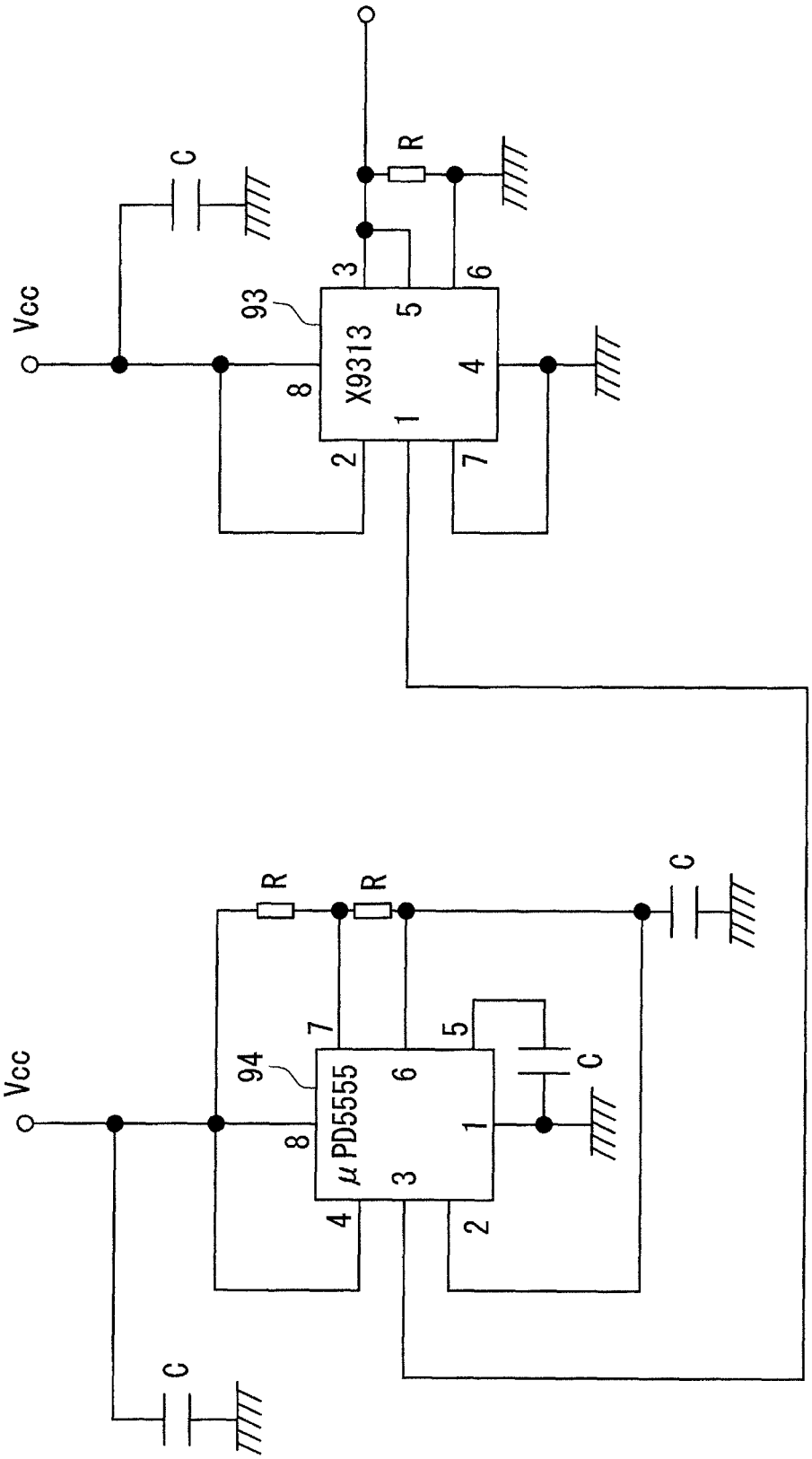
FIG. 6 is a circuit diagram illustrating wiring of a potentiometer and a timer.

As illustrated in FIG. 6, the setting of the resistances of the potentiometers 93 is performed by a timer IC94. The timer IC94 is driven by a constant voltage source Vcc (+5V) which outputs a constant voltage. Although not illustrated in the circuit diagram of FIG. 6, the constant voltage source Vcc becomes a constant voltage (+5V) when the power switch SW1 is turned ON. When the constant voltage source Vcc becomes a constant voltage, the timer IC94 outputs a preset number of pulses (rectangular wave). The pulses are input into the potentiometers 93. The potentiometers 93 count the number of the input pulses with a counter to exhibit a resistance according to the count value. Thus, the resistances of the potentiometers 93 are set by the timer IC94 whenever the power switch SW1 is turned ON. The timer IC94 is equivalent to the setting unit.

Six timers IC94 are provided in the casing 71 of the power supply body 70. One timer IC94 simultaneously sets the resistances of the two potentiometers 93 which are connected in parallel. More specifically, one timer IC94 sets the resistance of any one of the variable resistors VR2 to VR7. The variable resistors VR2 to VR7 each are set to the resistances which are different from each other by the six timers IC94. More specifically, when the knob 75 (FIG. 1) indicates "1", the resistance of the variable resistor VR2 which is connected in parallel to the direct-current motor M is set to the smallest resistance among the variable resistors VR2 to VR7. The resistance of the variable resistor VR3 is set to be higher than the resistance of the variable resistor VR2. The resistance of the variable resistor VR4 is set to be higher than the resistance of the variable resistor VR3. The resistance of the variable resistor VR5 is set to be higher than the resistance of the variable resistor VR4. The resistance of the variable resistor VR6 is set to be higher than the resistance of the variable resistor VR5. The resistance of the variable resistor VR7 is set to be higher than the resistance of the variable resistor VR6. Therefore, when the knob 75 is turned from "1" to "6", the resistances of the resistors (the variable resistors VR2 to VR7) connected to the circuit become higher in a stepwise manner. Thus, the output current of the three-terminal regulator 91 becomes higher in a stepwise manner, so that the rotation speed (unloaded state) of the direct-current motor M becomes higher in a stepwise manner.

The socket 72 illustrated in FIG. 5 is provided in such a manner that six batteries of a rated voltage of 3 V can be attached thereto. More specifically, the rated voltage of the battery E is 18V.

For the partial pressure resistor R1, a 18 kΩ resistor is used. For the partial pressure resistor R2, a 1.3 kΩ resistor is used. For the variable resistor VR1, a variable resistor whose maximum resistance is 50 kΩ is used. For the switching element Q, a general-purpose transistor 2SC945 manufactured by NEC Corp. (Registered Trademark) is used. For the three-terminal regulator 81, 78L05 manufactured by Digi-Key (Registered Trademark) is used. For the voltage regulation resistor R6, a 560Ω resistor is used.

For the resistors R3 and R4 constituting the protective circuit 83, a 10 kΩ resistor is used. For the resistor R5, a 4.7 MΩ resistor is used. For the capacitor C1, a 0.47 μF capacitor (capacitor) is used. For the NAND circuits 83A, U4011 which is a general-purpose logic IC is used.

For the three-terminal regulator 91, LT1085 manufactured by LINEAR TECHNOLOGY (Registered Trademark) is used. For the partial pressure resistor R7, a 180Ω resistor is used. The potentiometer 93 illustrated in FIG. 6 is X9313 of Xicor (Registered Trademark). The timer IC94 illustrated in FIG. 6 is μPD5555 of RENESAS (Registered Trademark). A resistor R and a capacitor C to be connected to the potentiometer 93 and the timer IC94 are set to the resistance and the capacity according to a specification of LT1085 and μPD5555.

Figure 4:
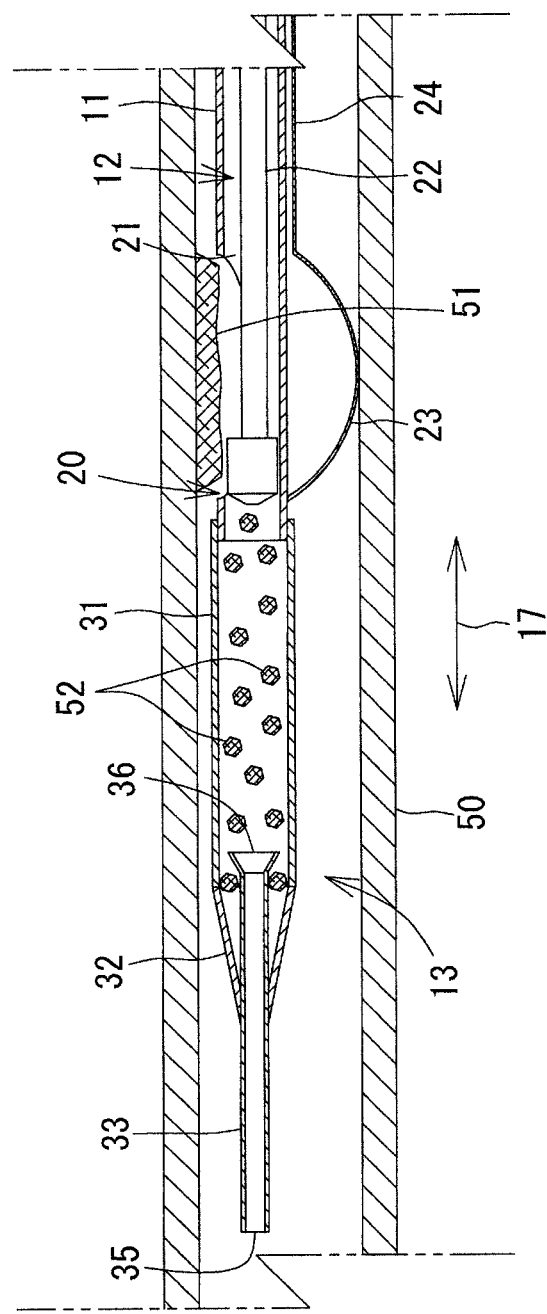
FIG. 4 is a schematic view illustrating a state where an atheroma is excised in the blood vessel.

Hereinafter, the directions for use of the atherectomy device 100 are described with reference to FIGS. 1, 3, and 4.

First, the knob 75 illustrated in FIG. 1 is turned to "1" so that the rotation speed of the direct-current motor M in an unloaded state is the lowest. The balloon 23 is contracted. The power switch SW1 (FIG. 5) is turned ON once to confirm that the voltage of the battery E is sufficiently high, and thereafter, the power switch SW1 is turned OFF.

Next, the distal end portion 13 of the catheter 10 is inserted into the blood vessel 50. Although not illustrated in each figure, when the distal end portion 13 is inserted into the blood vessel 50, a guide wire is inserted into the blood vessel 50 beforehand. The insertion of the guide wire into the blood vessel 50 is performed by a known technique. While the guide wire inserted into the blood vessel 50 being inserted into the internal space of the distal end tip 33 of the distal end portion 13, the internal space of the shaft 11, the through-hole of the cutting portion 21 of the cutter 12, and the internal space of the shaft 22 in the stated order, the distal end portion 13 of the catheter 10 is inserted into the blood vessel 50.

As illustrated in FIG. 3, when the distal end portion 13 reaches the atheroma 51, and then the opening 20 of the shaft 11 faces the atheroma 51, the insertion of the shaft 11 into the blood vessel 50 is ended. Thereafter, the guide wire is drawn out from the proximal end side of the atherectomy catheter 10. The direct-current motor is connected to the shaft 22 of the cutter 12.

As illustrated in FIG. 3, the balloon 23 in a contracted state is expanded by the fluid which is made to flow into the outer tube 24 from the port 41 in the state where the opening 20 of the shaft 11 faces the atheroma 51. When the expanded balloon 23 abuts to the inner wall of the blood vessel 50 opposite to the atheroma 51, the opening 20 is made to adhere to the atheroma 51, and a part of the atheroma 51 is put into the internal space of the shaft 11 from the opening 20.

Subsequently, the power switch SW1 is turned ON. Thus, the direct-current motor M is driven, and then the cutting portion 21 is rotated through the shaft 22 of the cutter 12. A user moves the shaft 22 is moved in a direction where the cutting portion 21 abuts to the atheroma 51. The user judges the hardness of the atheroma 51 based on a feeling given to the hand when the cutting portion 21 abuts to the atheroma 51. The hardness of the atheroma 51 varies depending on the calcification degree. When the user judges that the atheroma 51 is relatively soft, the user further moves the shaft 22 while the knob 75 (FIG. 1) is being set to "1" to press the cutting portion 21 against the atheroma 51 to excise the atheroma 51. When the user judges that the atheroma 51 is hard, the user turns the knob 75 to any one of "2" to "6" according to the hardness degree to increase the rotation speed (unloaded state) of the direct-current motor M. Thereafter, the user further moves the shaft 22 to press the cutting portion 21 against the atheroma 51 to excise the atheroma 51.

As illustrated in FIG. 3, pieces 52 of the excised atheroma 51 are collected through the blade tube 31 through the interior space of the shaft 11. When the excision of the atheroma 51 is completed, the balloon 23 is contracted, and then the catheter 10 is drawn out to be removed from the blood vessel 50.

In this embodiment, since the rotation speed of the cutting portion 21 can be made high according to the hardness of the atheroma 51, the atheroma 51 can be quickly excised. Moreover, the rotation speed of the cutting portion 21 can be instantly made high by switching the variable resistors VR2 to VR7 using the change-over switch SW2. As a result, the time required for the excision of the atheroma 51 can be shortened, so that the burden to a patient can be reduced.

Moreover, in this embodiment, since not a fixed resistor but the variable resistors VR2 to VR7 are used for the resistors to be connected in parallel to the direct-current motor M, the resistance of the resistors to be connected in parallel to the direct-current motor M can be easily adjusted according to a specification before delivery.

Moreover, in this embodiment, since the variable resistors VR2 to VR7 are constituted by the potentiometer 93, an increase in the error of the resistance due to changes with time can be suppressed as compared with a case of using a mechanical variable resistor in which a movable piece slides on a resistor. Moreover, since the variable resistors VR2 to VR7 are constituted by the potentiometer 93, a user can be prevented from accidentally changing the resistances of the variable resistors VR2 to VR7.

Moreover, in this embodiment, when the power switch SW1 is turned ON, the constant voltage source Vcc which drives the timer IC94 applies a constant voltage (+5V). Therefore, the resistance of the potentiometer 93 is set whenever the power switch SW1 is turned ON. Therefore, a state where the resistances of the variable resistors VR2 to VR7 are erroneously set is not maintained, and the safety is improved.

Moreover, in this embodiment, the socket 72 to which the battery E is attached is provided in the casing 71 of the power supply body 70. Therefore, the weight of the operation body 60 can be reduced according to the weight of the battery as compared with a casing where the socket 72 is provided in the operation body 60 held in the hand for use. As a result, the handling of the atherectomy device 100 is facilitated. Moreover, since a large capacity battery or a large number of batteries can be used, the period of time while the atherectomy device 100 can be continuously used can be prolonged.

Moreover, since the change-over switch SW2 is provided in the power supply body 70, the operation body 60 does not accidentally move when operating the change-over switch SW2.

Moreover, in this embodiment, it can be easily judged whether the voltage of the battery E is sufficiently high for using the atherectomy device 100 based on lighting on or off of the light emitting diode LED.

Moreover, in this embodiment, since the variable resistor VR1 is used for the partial pressure resistor circuit 82 which turns ON/OFF the switching element Q, a reduction degree of the voltage of the battery E based on which it is judged that the light emitting diode LED is lighted off can be easily adjusted according to a specification before delivery and the like.

The above-described embodiment describes the configuration in which the resistor group 92 having the variable resistors VR2 to VR7 and the change-over switch SW2 are provided in the power supply body 70. However, the resistor group 92 and the change-over switch SW2 may be provided in the operation body 60. When the operation body 60 held in the hand for use is provided with the change-over switch SW2, it is not required to place the power supply body 70 near the user, so that the user-friendliness of the atherectomy device 100 is improved.

Moreover, the above-described embodiment describes the configuration in which the power supply body 70 to which the battery is attached and the operation body 60 held in the hand for use are separated. However, the power supply body 70 and the operation body 60 may be integrated. Specifically, the socket 72, the power switch SW1, the detection circuit 80, the drive circuit 90, and the direct-current motor M are provided in the operation body 60. In this modification, although the weight becomes higher than the weight in the case of the above-described embodiment, the cable 16 is not required to be connected to the operation body 60. Since the cable 16 is not required to be connected to the operation body 60, the handling of the atherectomy device 100 is facilitated.

Moreover, the above-described embodiment describes the configuration in which the six variable resistors VR2 to VR7 are used. However, 2 to 5 or 7 or more variable resistors may be used. Moreover, a plurality of fixed resistors whose resistances are different from each other may be used in place of the variable resistors. The use of the fixed resistor reduces the manufacturing cost of the atherectomy device 100.

Moreover, the above-described embodiment describes the configuration in which the rotary switch is used for the change-over switch SW2. However, a slide switch may be used for the change-over switch SW2.

Moreover, the above-described embodiment describes the configuration in which the light emitting diode LED is used to notify a voltage reduction of the battery E. However, a speaker or a display panel may be used in place of the light emitting diode LED. When a speaker is used, a voltage reduction of the battery E is reported by a sound. When a display panel is used, a voltage reduction of the battery E is reported by characters or figures (pictures) to be displayed in the display panel.

Moreover, the above-described embodiment describes the configuration in which the socket 72 is provided in the power supply body 70. However, an AC-DC converter which converts an alternating current to a direct current to output the same may be provided in place of the socket 72. In this case, the detection circuit 80 is not required.

Moreover, the above-described embodiment describes the configuration in which the change-over SW2 is provided between the resistor group 92 and the negative electrode terminal 72B of the socket 72. However, the change-over SW2 may be provided between the partial pressure resistor R7 and the resistor group 92.

Moreover, the above-described embodiment describes the configuration in which the light emitting diode LED is lighted on by a direct current to be supplied from the battery E through the three-terminal regulator 81. However, a battery which supplies a direct current to the light emitting diode LED may be provided in the casing 71 separately from the battery E. Also in this configuration, the light emitting diode LED is lighted on or off by the ON/OFF of the switching element Q.

The resistors and the variable resistors in the above-described embodiment may be configured by a single resistor element or may be configured as a combined resistor of a plurality of resistor elements.

Figure 7:
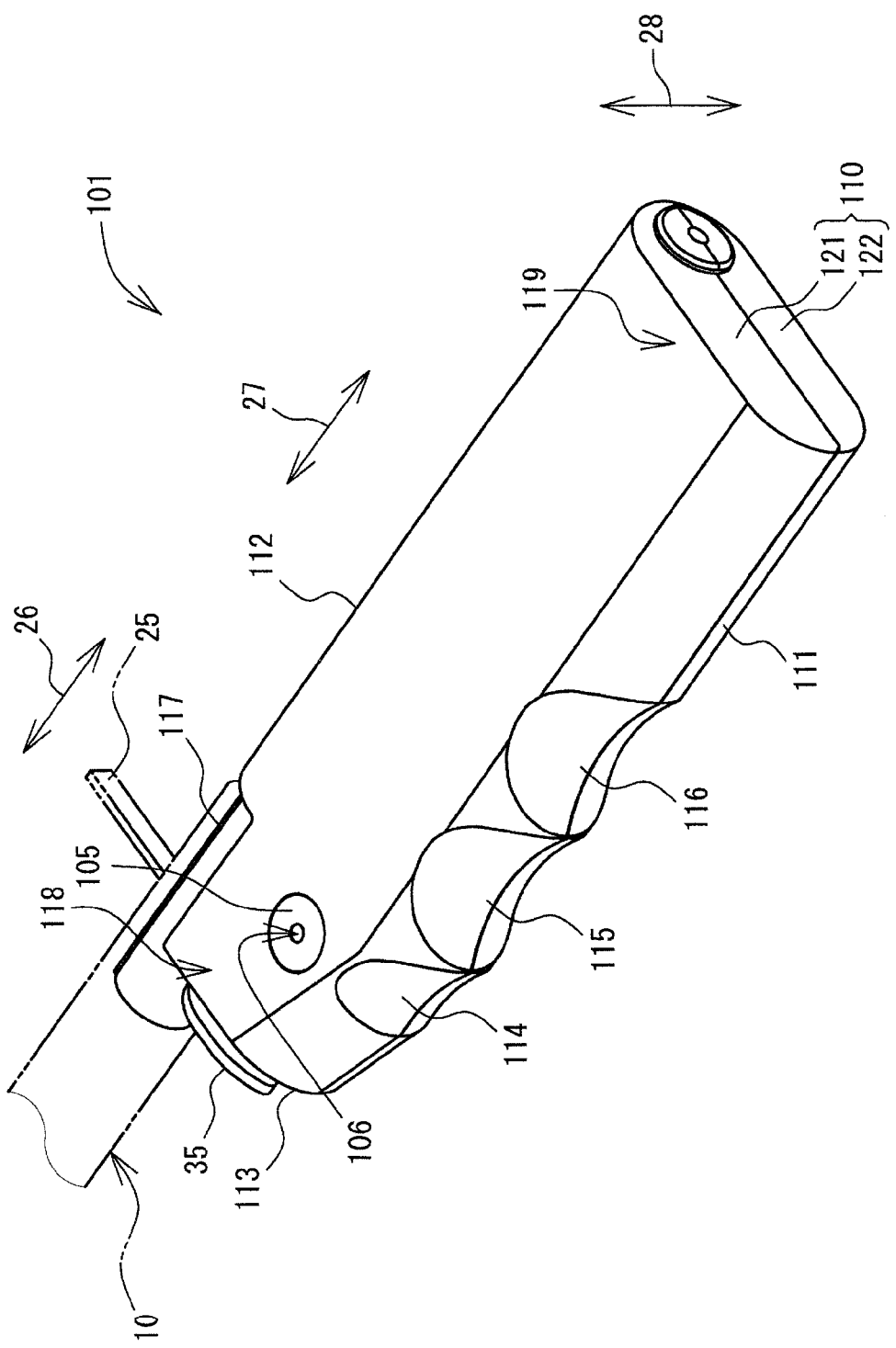
FIG. 7 is a perspective view of the appearance of the left surface side of an atherectomy device of a second embodiment.

This embodiment describes an atherectomy device 101 illustrated in FIG. 7. The atherectomy device 101 is an integral-type device in which a battery E1 (FIG. 13) is included in a bodycasing 110. In the following description, the same reference numerals are given to the same configuration as those of the first embodiment and a description thereof is omitted.

Figure 13:
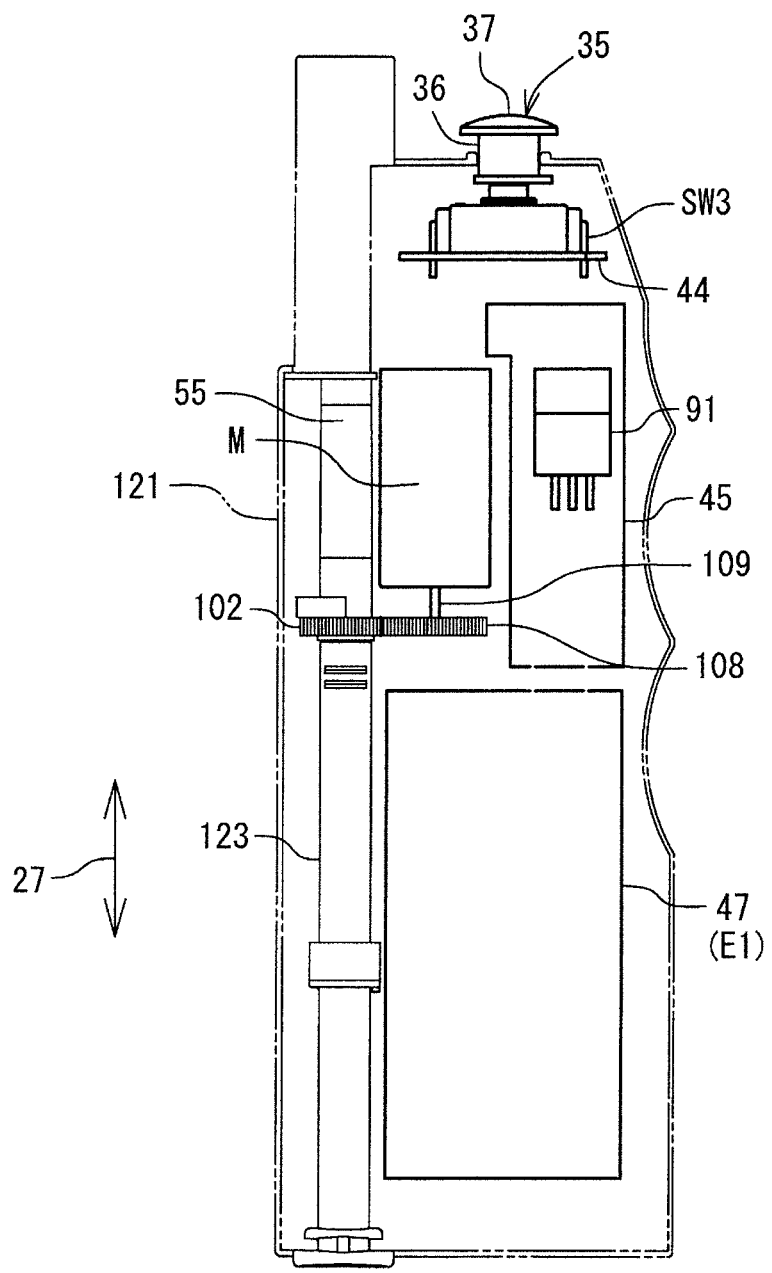
FIG. 13 is a schematic view of the inside of the atherectomy device.

A user attaches the middle finger, the third finger, and the little finger to dents 114, 115, and 116 of the bodycasing 110, and holds the atherectomy device 101. The user presses a push button 35 using the index finger to turn ON/OFF a power switch SW3 (FIG. 13). The user makes a slide bar 25 of the catheter 10 slide in a sliding direction 26 using the thumb. The slide bar 25 is synchronized with the cutter 12 (FIG. 2). More specifically, the user turns ON the power switch SW3 using the index finger to rotate the cutter 12, and then make the slide bar 25 slide using the thumb to press the cutter 12 against an atheroma to excise the atheroma. Thus, the atherectomy device 101 of this embodiment can be used with a single hand (right hand).

As illustrated in the perspective views and six surface views of FIG. 7 to FIG. 12, the bodycasing 110 has an outer shape of a flat and narrow and long rectangular parallelepiped which allows a user to hold the same with a single hand. In a first side wall 111 along a longitudinal direction 27 and a thickness direction 28 of the bodycasing 110, the dents 114, 115, and 116 where the middle finger, the third finger, and the little finger of the user are attached are formed. More specifically, the entire bodycasing 110 serves as a grip.

The bodycasing 110 is assembled by combining two parts of a base 121 and a cover 122 in such a manner that the power supply substrate 45, the direct-current motor M (FIG. 13), and the like can be disposed in the internal space. The base 121 and the cover 122 have an outer shape in which the bodycasing 110 is divided into equal parts in the thickness direction 28.

Figure 8:
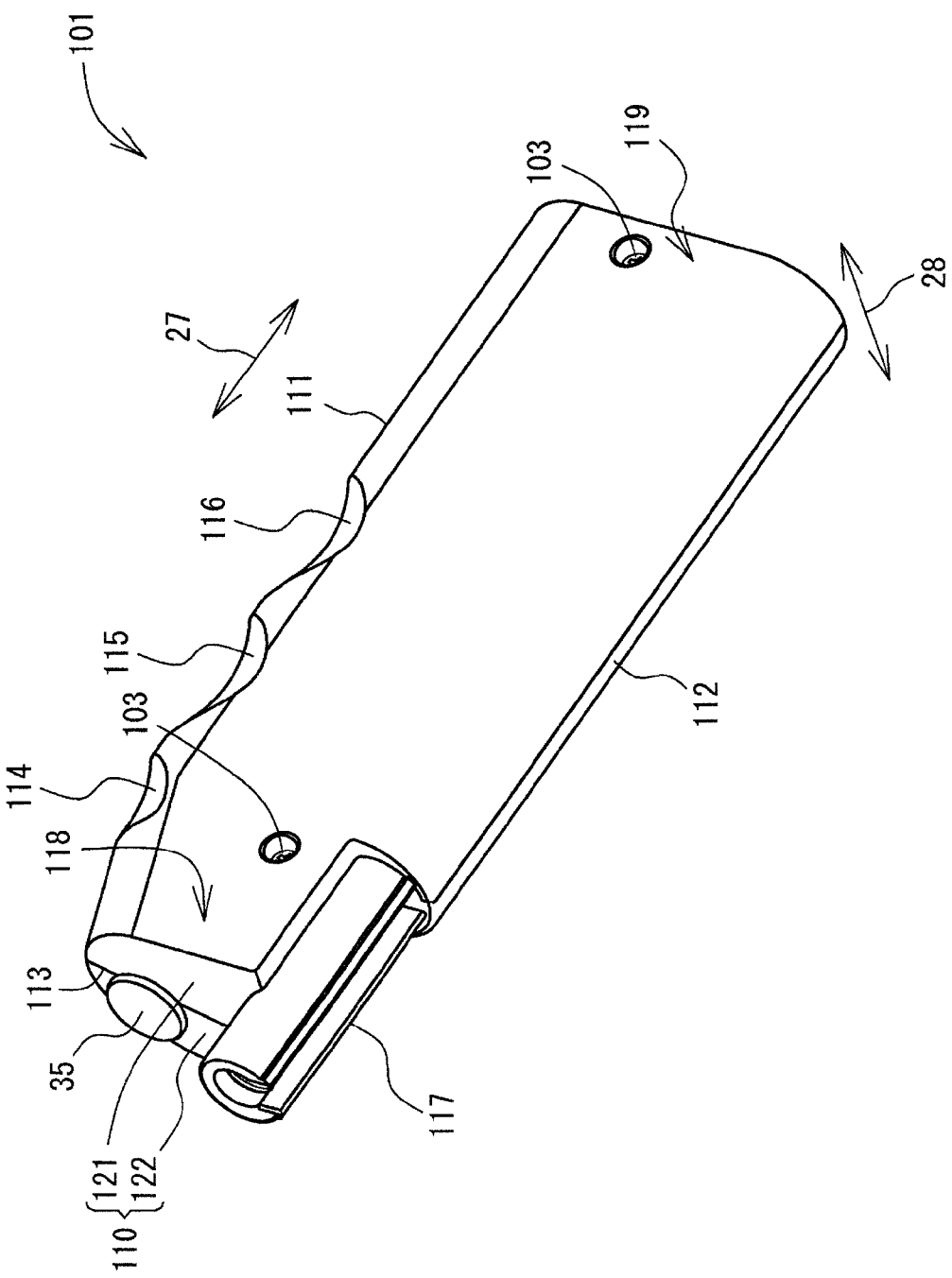
FIG. 8 is a perspective view of the appearance of the right surface side of the atherectomy device.
Figure 9:
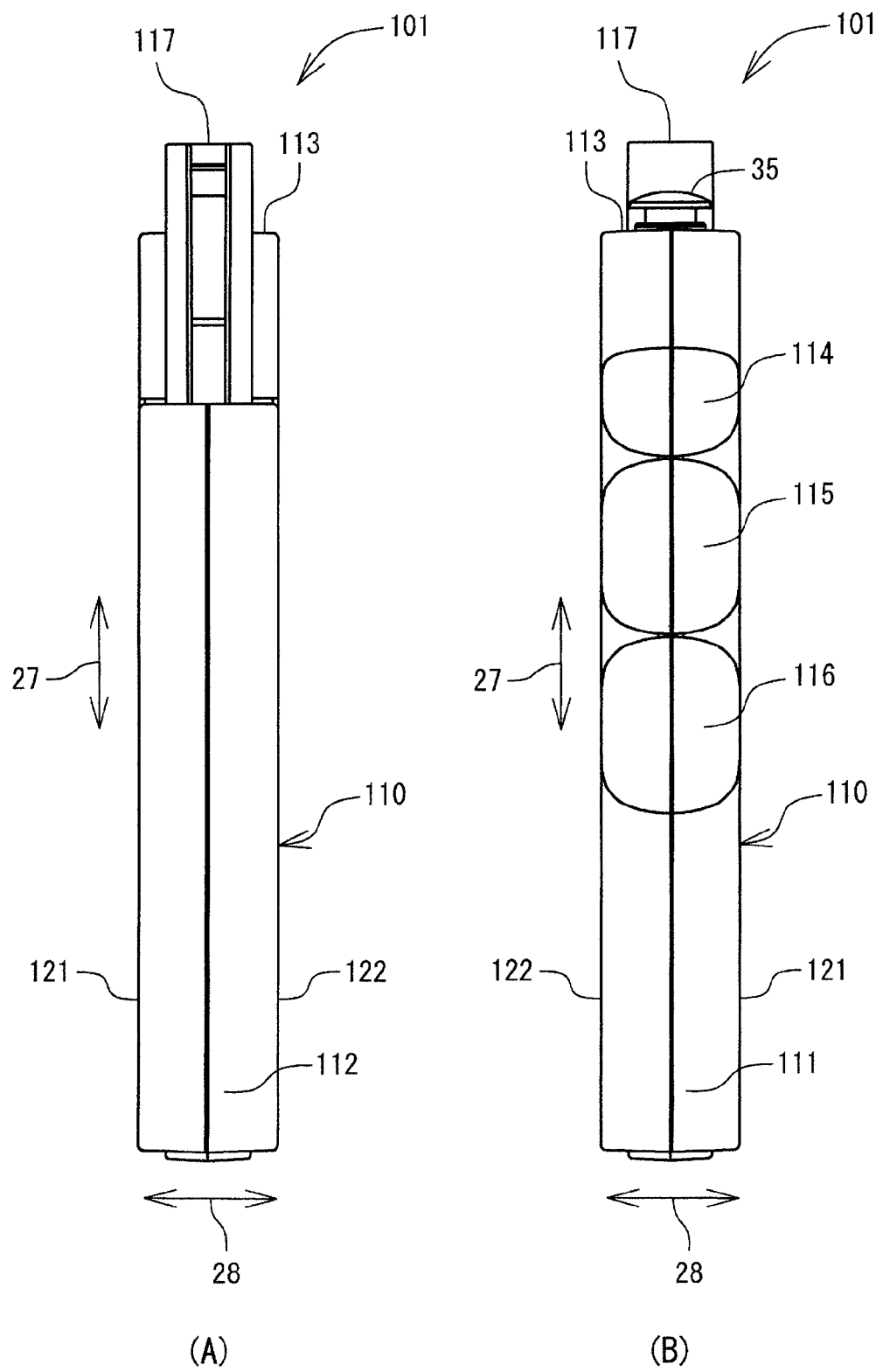
FIG. 9(A) is a front view of the atherectomy device and FIG. 9(B) is a rear view of the atherectomy device.
Figure 10:
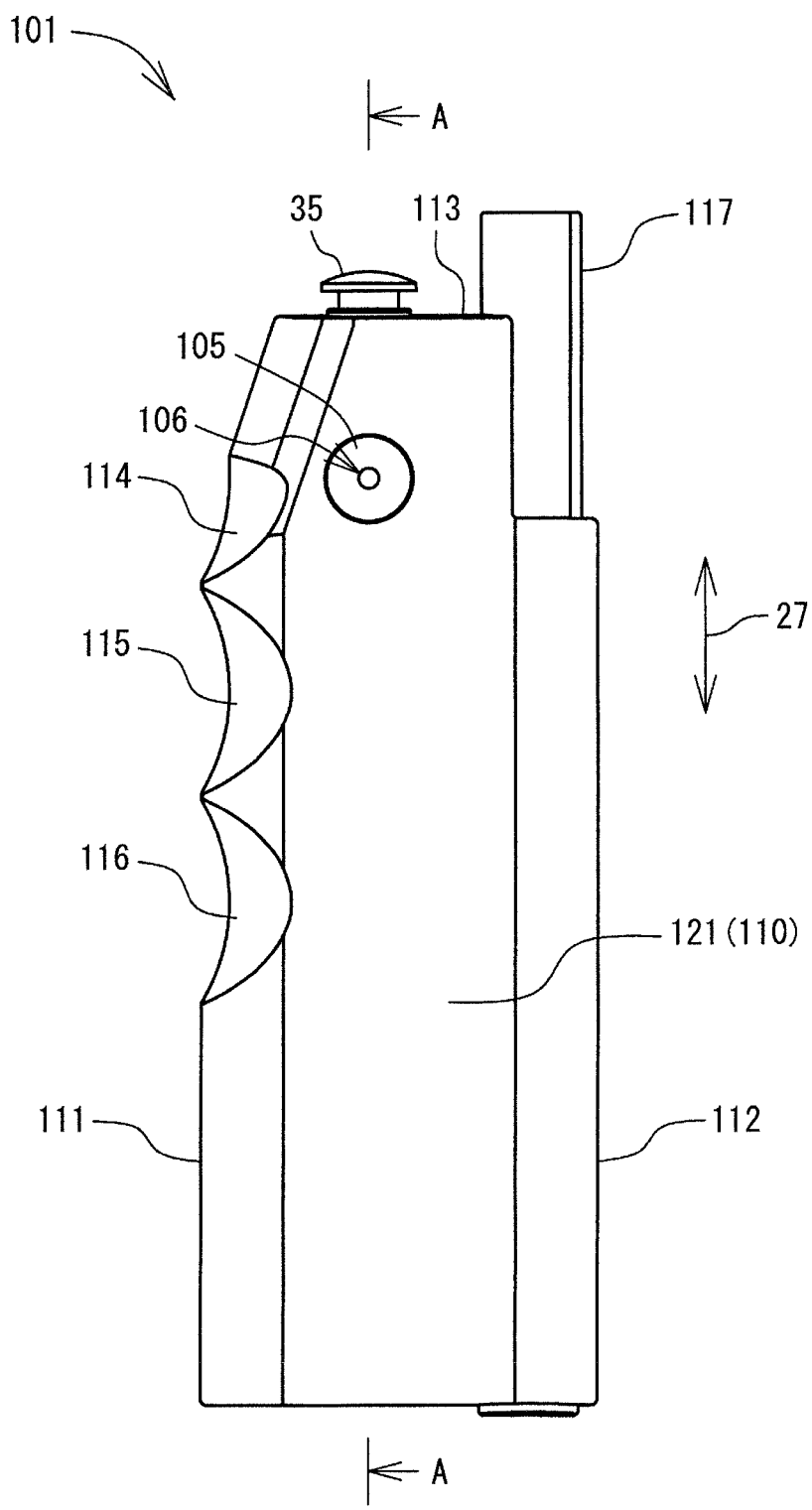
FIG. 10 is a left side view of the atherectomy device.
Figure 11:
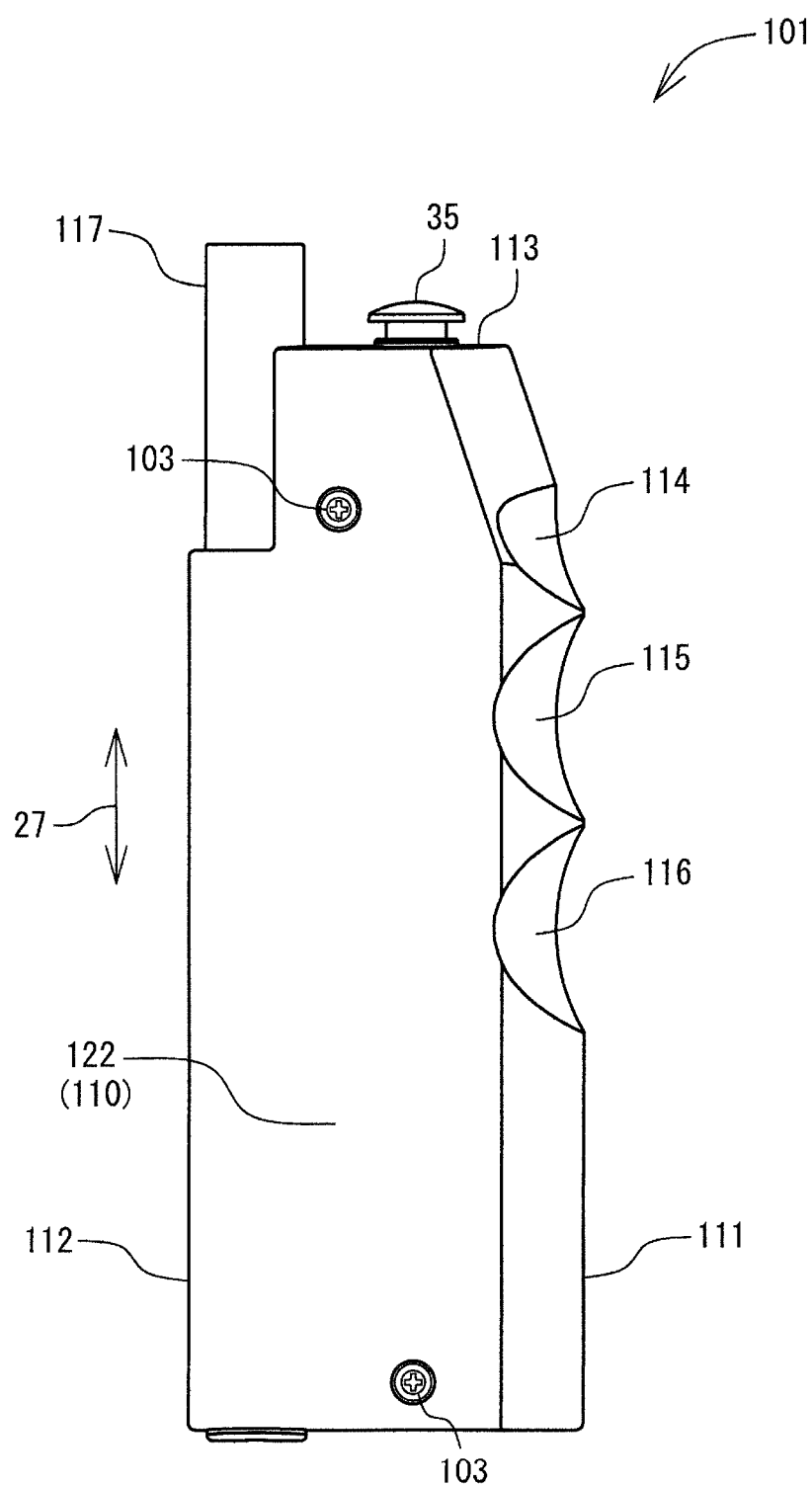
FIG. 11 is a right side view of the atherectomy device.
Figure 12:
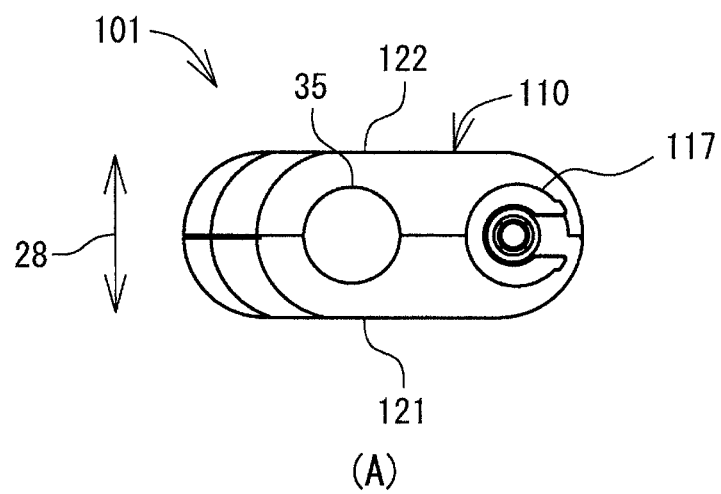
FIG. 12(A) is a plan view of the atherectomy device and FIG. 12(B) is a bottom view of the atherectomy device.
Figure 12:
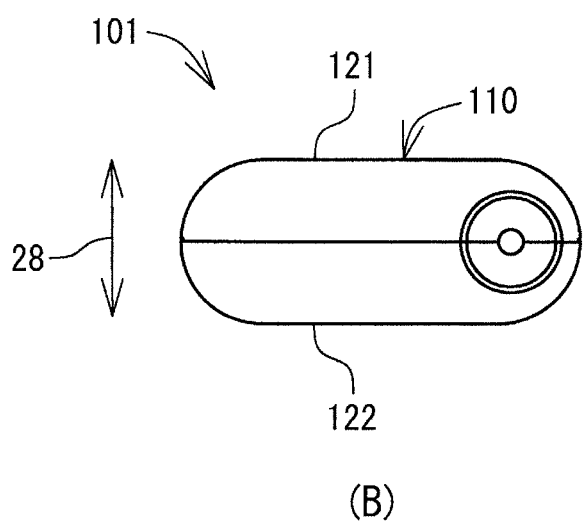

As illustrated in FIG. 8, the cover 122 is secured to the base 121 by two screws 103. Specifically, the cover 122 is provided with two openings (not illustrated) through which the screws 103 are passed. On the other hand, two screw holes (not illustrated) into which the screws 103 are screwed are formed in the base 121. The cover 122 is placed over the base 121 after disposing the power supply substrate 45, the direct-current motor M, and the like in the base 121, and then secured to the base 121 by the two screws 103.

Between the base 121 and the cover 122, a waterproofing measure is provided. The waterproofing measure refers to, for example, a rib and a groove provided almost over the entire circumference of the peripheral edge of the base 221 and the cover 122. The waterproofing is realized by engagement of the rib and the groove. Or, the waterproofing may be realized using packing, an adhesive, and the like disposed between the base 121 and the cover 122.

As illustrated in FIG. 7, the bodycasing 110 is provided with a connection tube 117 (equivalent to the connection portion) onto which the catheter 10 is fitted. The connection tube 117 is provided at a position where when a user holds the bodycasing 110, the thumb can be attached to the slide bar 25. Specifically, the connection tube 117 is provided on the side of a first end portion 118 which is one end in the longitudinal direction 27 and the side of a second side wall 112 opposite to the first side wall 111 in such a manner that the axial direction is in agreement with the longitudinal direction 27.

As illustrated in FIG. 13, a joint 123 is disposed in the bodycasing 110. When the slide bar 25 is made to slide, a part of the catheter 10 moves into/out of the joint 123. The joint 123 is formed into a cylindrical shape extending along the longitudinal direction 27 and is disposed at the deep side (lower side in FIG. 13) of the connection tube 117.

Next to the connection tube 117 (right side in FIG. 13), the direct-current motor M is disposed. The direct-current motor M is disposed in such a manner that the axial direction of the shaft 109 is in agreement with the longitudinal direction 27. To the shaft 109, a gear 108 adheres. The gear 108 is engaged with a gear 102 rotatably disposed in the connection tube 117. The gear 102 is synchronized with the cutter 12 through a rotation shaft 55. Thus, the driving force of the direct-current motor M is transmitted to the cutter 12 through the gears 102 and 108 and the rotation shaft 55, so that the cutter 12 is rotated. The drive of the direct-current motor M is turned ON/OFF by the power switch SW3 through the push button 35.

Figure 14:
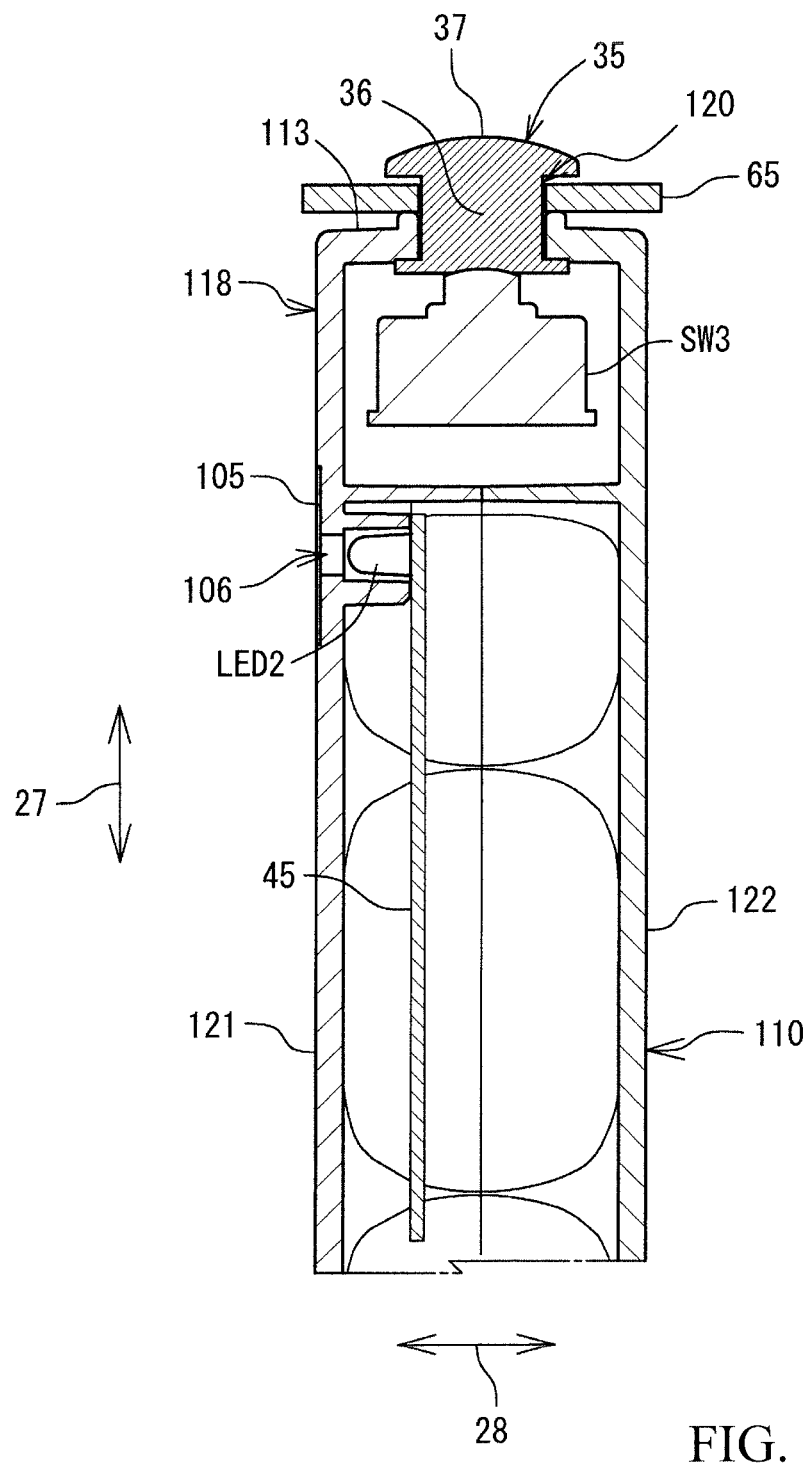
FIG. 14(A) is an enlarged top view of the A-A cross section of FIG. 10.

As illustrated in FIG. 13 and FIG. 14, the push button 35 is fitted into an opening 120 of the bodycasing 110. The opening 120 is opened in a third side wall 113 on the first end portion 118 side of the bodycasing 110. Between the edge of the opening 120 and the push button 35, a packing for waterproofing may be disposed. When the push button 35 is not pressed, the packing is stuck to the edge of the push button 35 and the opening 120 to prevent water from entering the bodycasing 110 from the opening 120.

The power switch SW3 is disposed at the deep side (lower side in FIG. 14) of the push button 35 and is mounted and fixed to the switch substrate 44. When the push button 35 is pressed by a user, an operation portion of the power switch SW3 is pressed by the push button 35.

For the power switch SW3, an alternate type (push-on/push-off type) push switch in which ON and OFF are switched whenever the power switch SW3 is pressed is used considering user-friendliness. However, a slide switch, a lever switch, a momentary type push switch, and the like may be used as the power switch SW3. The power switch SW3 is electrically connected to a power supply substrate 45 through a lead wire.

As illustrated in FIG. 14, the push button 35 has a shaft portion 36 passed through the opening 120 and an operation portion 37 disposed on the outside of the bodycasing 101. A clearance is formed between the operation portion 37 and the third side wall 113 of the bodycasing 101. In the clearance, a stopper 65 may be stationed.

The drive of the direct-current motor M can be confirmed by lighting on of a light emitting diode LED2. A detailed description is given below. As illustrated in FIG. 7, the dent 105 slightly (several millimeters) dented from the outer surface of the base 121 is formed on the first end portion 118 side of the base 121. To the dent 105, an identification plate having translucency, which is not illustrated, is stuck. In the central portion of the dent 105, a through-hole 106 is opened. As illustrated in FIG. 14, the light emitting diode LED2 is disposed at the deep side (right side in FIG. 14) of the through-hole 106. The light emitting diode LED2 is lighted on when the direct-current motor M is driven as described later.

A user confirms lighting on and lighting off the light emitting diode LED2 through the through-hole 106 and the translucent identification plate to thereby confirm the drive of the direct-current motor M (FIG. 13). The dent 105 is formed in the base 121 in order that when the user holds the atherectomy device 101 with the right hand, the light emitting diode LED2 is prevented from being covered with the hand.

Figure 15:
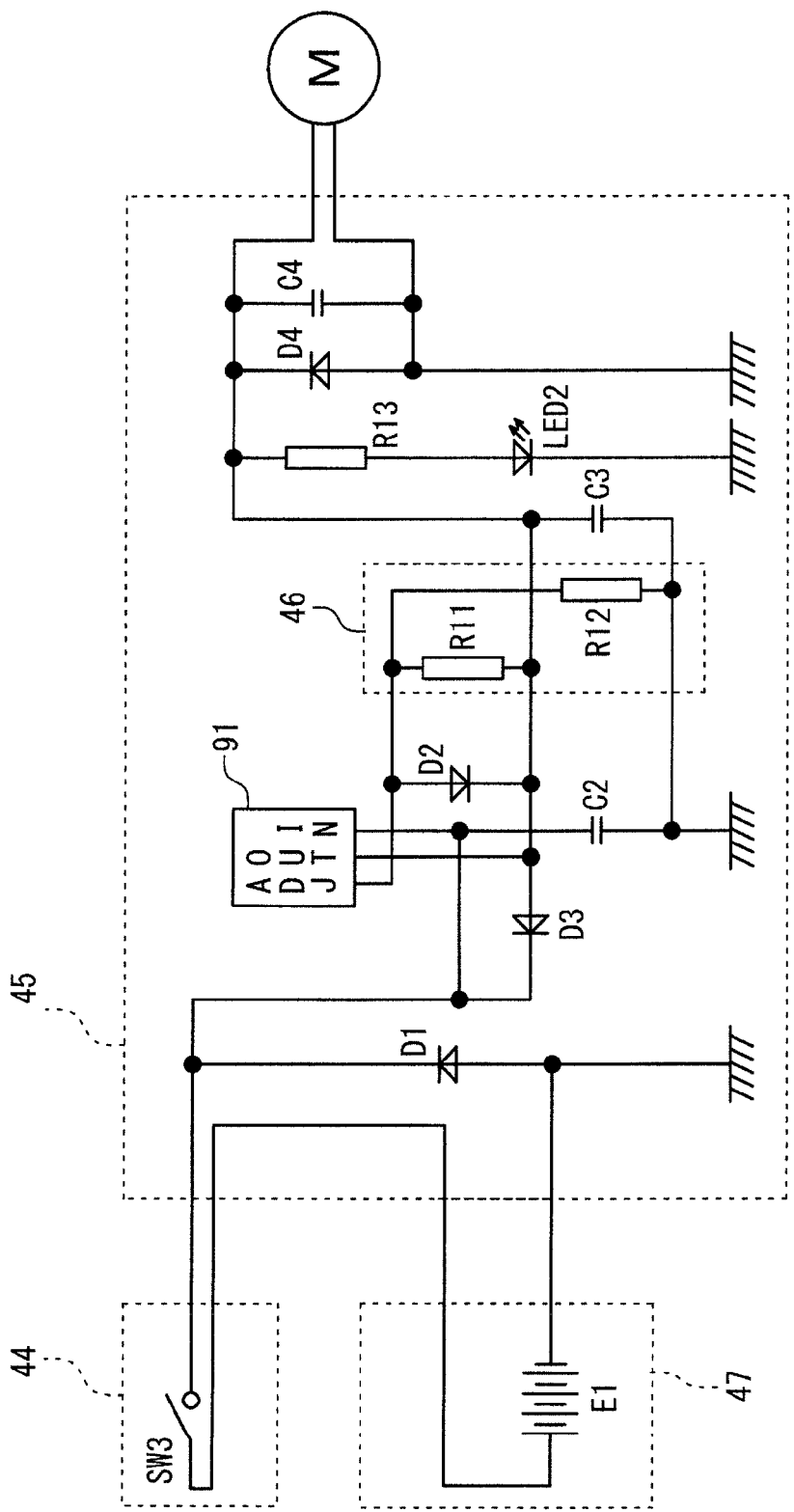
FIG. 15 is a circuit diagram of the atherectomy device.

The light emitting diode LED2 and the direct-current motor M are driven by a power supply 47 (FIG. 15) containing the battery E1. The power supply 47 has a voltage of 6 to 30 V and preferably 9 to 12 V. The power supply 47 is used in order that a voltage (12 V) equal to or higher than the rated voltage (9V) of the direct-current motor M is used as the power supply 47 and the drive time (for example, 5000 seconds) of the direct-current motor M required for the atheroma excision is secured.

As illustrated in FIG. 13, the power supply substrate 45 is disposed in the bodycasing 110. The power supply substrate 45 is disposed between a switch substrate 44 and the battery E1 in the longitudinal direction 27 and next to the direct-current motor M (right side in FIG. 13(A)).

As illustrated in FIG. 13 and FIG. 14, various electronic components, such as the three-terminal regulator 91 and the light emitting diode LED2 (FIG. 14), are mounted in the power supply substrate 45. Hereinafter, a circuit of FIG. 15 constituted by the battery E1, the switch substrate 44, and the power supply substrate 45 is described in detail. In the following description, "connected" means "electrically connected by a pattern (printed wiring) and a lead wire of the switch substrate 44 and the power supply substrate 45.

The power supply 47 (battery E1) is connected to the power supply substrate 45. One terminal of the power switch SW3 is connected to the power supply 47 in the power supply substrate 45 and the other terminal is connected to an input terminal (IN) of the three-terminal regulator 91. Therefore, the input of a voltage from the power supply 47 to the three-terminal regulator 91 can be turned ON/OFF by ON/OFF of the power switch SW3.

In the power supply substrate 45, a protection diode D1 which protects the three-terminal regulator 91 and the like is mounted. The anode of the protection diode D1 is connected to the power supply 47 and the cathode of the protection diode D1 is connected to the input terminal (IN) of the three-terminal regulator 91. The protection diode D1 prevents the reverse current of a current to protect the three-terminal regulator 91 and the like.

Between the output terminal (OUT) and the ADJ terminal of the three-terminal regulator 91, a partial pressure circuit 46 which determines the output voltage of the three-terminal regulator 91 is connected. The partial pressure circuit 46 is a circuit which divides the output voltage of the three-terminal regulator 91 to input the same into the ADJ terminal of the three-terminal regulator 91.

The partial pressure circuit 46 is constituted by partial pressure resistors R11 and R12 mounted in the power supply substrate 45. One end of the partial pressure resistor R11 is connected to the ADJ terminal of the three-terminal regulator 91 and the other end of the partial pressure resistor R11 is connected to the output terminal (OUT) of the three-terminal regulator 91. One end of the partial pressure resistor R12 is connected to the ADJ terminal of the three-terminal regulator 91 and the other end of the partial pressure resistor R12 is grounded (virtual ground). Thus, the ADJ terminal of the three-terminal regulator 91 is connected to the partial pressure resistor R11 and the partial pressure resistor R12. The partial pressure circuit 46 regulates the output voltage of the three-terminal regulator 91 based on the ratio of the resistance of the partial pressure resistor R11 and the resistance of the partial pressure resistor R12. Based on the voltage input into the ADJ terminal, the three-terminal regulator 91 outputs a constant voltage irrespective of the size of a load (resistance of the direct-current motor M). The resistances of the partial pressure resistor R11 and R12 are set in such a manner that the three-terminal regulator 91 outputs 9 V which is the rated voltage of the direct-current motor M.

Moreover, capacitor C2 and C3 and diodes D2 and D3 are connected to the three-terminal regulator 91 for circuit protection and the like. The capacitor C2 is mounted in the power supply substrate 45, is grounded at one end (virtual ground), and is connected to the input terminal (IN) of the three-terminal regulator 91 at the other end. The capacitor C3 is mounted in the power supply substrate 45, is grounded (virtual ground) at one end, and is connected to the output terminal (OUT) of the three-terminal regulator 91 at the other end. The diode D2 is mounted in the power supply substrate 45, is connected to the ADJ terminal of the three-terminal regulator 91 at the anode, and is connected to the output terminal (OUT) of the three-terminal regulator 91 at the cathode. The diode D3 is mounted in the power supply substrate 45, is connected to the output terminal (OUT) of the three-terminal regulator 91 at the anode, and is connected to the input terminal (IN) of the three-terminal regulator 91 at the cathode.

Moreover, the light emitting diode LED2 for confirming of the operation is connected to the output terminal (IN) of the three-terminal regulator 91 through a protection resistor R13. Specifically, the protection resistor R13 is mounted in the power supply substrate 45, is connected to the output terminal (OUT) of the three-terminal regulator 91 at one end, and is connected to the anode of the light emitting diode LED2 at the other end. The cathode of the light emitting diode LED2 is grounded (virtual ground). When the power switch SW3 is turned ON, the direct-current motor M is driven and also the light emitting diode LED2 is lighted on.

The output terminal (OUT) of the three-terminal regulator 91 is connected to one end of the input terminal of the direct-current motor M through the pattern and a lead wire of the power supply substrate 45. The other end of the input terminal of the direct-current motor M is grounded (virtual ground) in the power supply substrate 45.

A protection diode D4 is mounted in the power supply substrate 45. The protection diode D4 is connected in parallel to the direct-current motor M.

Moreover, a capacitor C4 which protects the circuit and suppresses changes in the input voltage of the direct-current motor M is mounted in the power supply substrate 45. The capacitor C4 is connected in parallel to the direct-current motor M.

A user attaches the right middle finger, the third finger, and the little finger to the dents 114, 115, and 116, attaches the index finger to the push button 35, attaches the thumb to the slide bar 25, and then holds the bodycasing 110 with the right hand. The user performs the same operation as that in the case of Embodiment 1 to expand the balloon 23 (FIG. 3), and then puts a part of the atheroma 51 into the internal space of the shaft 11 from the opening 20 (FIG. 2).

Next, the user presses the push button 35 using the index finger to turn ON the power switch SW3 to thereby drive the direct-current motor M. In this case, 9 V which is the rated voltage is input into the direct-current motor M from the three-terminal regulator 91, and then the direct-current motor M is driven at the rated voltage.

The user who pressed the push button 35 confirms that the direct-current motor M is driven by the lighting on of the light emitting diode LED2. The user who confirmed that the direct-current motor M is driven makes the slide bar 25 slide using the thumb to presses the cutter 12 against the atheroma 51 to excise the atheroma 51.

The user who excised the atheroma 51 presses the push button 35 using the index finger to turn OFF the power switch SW3 to stop the drive of the direct-current motor M. The user confirms that the direct-current motor M has stopped based on the fact that the light emitting diode LED2 is lighted off.

In one operation, the above-described atheroma excision is performed several times. When the operation is completed, the used atherectomy device 101 is discarded, for example. More specifically, an unused atherectomy device 101 is used for each operation.

The rated voltage (9V) can be input into the direct-current motor M by the use of the three-terminal regulator 91 and the partial pressure circuit 46. Therefore, as compared with the configuration in which a battery is directly connected to a direct-current motor, the occurrence of a failure of the direct-current motor M can be suppressed and exhaustion of the battery E1 can be suppressed. By suppressing the exhaustion of the battery E1, the available time is prolonged or the size of the atherectomy device 101 can be reduced using a small capacity battery. Moreover, since the direct-current motor M is not driven at a voltage less than rated voltage, an atheroma can be certainly excised.

Moreover, since the power supply 47 (battery E1), the power switch SW3, the direct-current motor M, and the power supply substrate 45 are disposed in the bodycasing 110, it is not required to connect a cable to the bodycasing 110, a user can freely move the atherectomy device 101 held in the hand, and the user-friendliness of the atherectomy device 101 is good.

Moreover, since the three-terminal regulator 91 is used, the size of the atherectomy device 101 is reduced rather than a case where a switching regulator is used. A detailed description is given below. In general, the three-terminal regulator is more easily configured and is smaller than the switching regulator. However, the heat generation amount of the three-terminal regulator is higher than that of the switching regulator, and the three-terminal regulator is generally used with a heat dissipation unit, such as a heat sink. Thus, in general, when the three-terminal regulator is used, the device size increases due to the heat dissipation unit. In the three-terminal regulator, unless the heat dissipation unit is used, the amount of a load current which can be output from the three-terminal regulator (maximum output current value) decreases with an increase in the temperature. In this embodiment, it was confirmed that the amount of the load current which can be output from the three-terminal regulator 91 in the case where the heat dissipation means is not used is larger than the amount of a current required for the atheroma excision, and the direct-current motor M can be certainly rotated. More specifically, it was confirmed that, in the bodycasing 110 of a size which allows a user to hold the same in the hand for use, even when the heat dissipation unit (heat sink) is not used, the direct-current motor M can be sufficiently rotationally driven. Therefore, by the use of the three-terminal regulator 91, the size of the power supply substrate 45 is reduced, so that the size of the atherectomy device 101 can be reduced.

Although the switching regulator and the three-terminal regulator are the same in the respect that the regulators are electronic components which output a constant voltage, the regulators have advantages and disadvantages resulting from the difference in the operation principle. Therefore, in all the devices, the switching regulator is not always compatible with the three-terminal regulator without problems. On the other hand, when the three-terminal regulator is used in place of the switching regulator and the heat dissipation unit (heat sink and the like) is provided, the size of the device increases. Therefore, the use of the three-terminal regulator does not always directly lead to a reduction in the size of the device. In this embodiment, it was confirmed that the use of the three-terminal regulator 91 can reduce the size of the atherectomy device 101 in terms of the size of the atherectomy device 101, the power of the required direct-current motor M, the required drive time of the direct-current motor M, and the like.

Since the size of the atherectomy device 101 can be reduced and there is no cable, the atherectomy device 101 can be freely moved. Moreover, since the direct-current motor M is not driven at a voltage less than the rated voltage, an atheroma is certainly excised for a short time.

Moreover, by connecting a capacitor C4 in parallel to the direct-current motor M in addition to the three-terminal regulator 91, changes in the input voltage to the direct-current motor M can be more efficiently suppressed to the resistance of the direct-current motor M which sharply changes before and after the atheroma excision.

Moreover, the light emitting diode LED2 can facilitate the confirmation of the operation of the direct-current motor M. A detailed description is given below. When an operation sound of the direct-current motor M is small when the light emitting diode LED2 is not provided, it cannot be easily judged whether the direct-current motor M is rotating. Due to the fact that the light emitting diode LED2 is provided, it can be easily confirmed whether the direct-current motor M is rotating not by the sound of the direct-current motor M but by lighting on or off of the light emitting diode LED2. Thus, pressing the cutter 12 against an atheroma in a state where the direct-current motor M is not driven is suppressed. Moreover, the direct-current motor M is prevented from being accidentally continuously driven until the following atheroma is excised after the first atheroma is excised. As a result, the battery E1 is prevented from being unnecessarily exhausted.

Moreover, the judgment of the cause of a fault is facilitated by the light emitting diode LED2. A detailed description is given below. For example, it is supposed that a fault in which the direct-current motor M does not rotate even when the power switch SW3 is turned ON occurs in the manufacturing line. In this case, when the light emitting diode LED2 is lighted on, it can be judged that a fault of the direct-current motor M arises or the connection between the direct-current motor M and the power supply substrate 45 is poor. When the light emitting diode LED2 is not lighted on, it can be judged that a fault of the mounted parts, such as the three-terminal regulator 91 and the power switch SW3, arises or the connection between the switch substrate 44 and the power supply substrate 45 is poor. Thus, the judgment of the cause of the fault is facilitated by lighting on or off of the light emitting diode LED2.

Moreover, a stopper 65 (FIG. 14) prevents the power switch SW3 from being accidentally turned ON before use. As described above, for the power switch SW3, one in which ON/OFF are switched whenever the switch is pressed. Therefore, when the power switch SW3 is accidentally turned ON under transportation or the like, the direct-current motor M is continuously driven, so that the battery E1 is exhausted. Due to the fact that the stopper 65 is provided, the battery remaining amount of the battery E1 of an unused atherectomy device 101 is certainly secured.

The second embodiment describes the example in which the light emitting diode LED2 is used. However, other light emitting elements, such as a neon lamp, may be used in place of the light emitting diode LED2.

Moreover, the second embodiment describes the example in which two substrates of the switch substrate 44 and the power supply substrate 45 are provided. However, the power switch SW3 is mounted in the power supply substrate 45 and the switch substrate 44 may be omitted.

REFERENCE SIGNS LIST

10 . . . Catheter
12 . . . Cutter
16 . . . Cable
45 . . . Power supply substrate (Substrate)
46 . . . Partial pressure circuit
60 . . . Operation body
61 . . . Casing (First casing)
62 . . . Grip
70 . . . Power supply body
71 . . . Casing (Second casing)
72 . . . Socket
80 . . . Detection circuit
82 . . . Partial pressure resistance circuit
91 . . . Three-terminal regulator
92 . . . Resistance group
93 . . . Potentiometer
94 . . . Timer IC (Setting unit)
100, 101 . . . Atherectomy device
110 . . . Bodycasing
117 . . . Connection tube (Connection portion)
E, E1 . . . Battery
M . . . Direct-current motor
R7 . . . Partial pressure resistor
SW2 . . . Change-over switch
SW3 . . . Power switch
VR1 to VR7 . . . Variable resistor
Q . . . Switching element
LED . . . Light emitting diode (Notification portion)
LED2 . . . Light emitting diode (Light emitting element)

The invention claimed is:

1. An atherectomy device to which a catheter having a tubular body having an opening in a side wall and a cutter which is provided movably in an axial direction in the tubular body is connected, the atherectomy device, comprising:
a direct-current motor which rotates the cutter;
a three-terminal regulator which has an input terminal, an output terminal, and an ADJ terminal and in which one of a pair of input terminals of the direct-current motor is connected to the output terminal;

a partial pressure resistor connected between the output terminal and the ADJ terminal of the three-terminal regulator;

a resistor group having a plurality of fixed resistors or a plurality of variable resistors whose resistances are different from each other and one end of which is connected to the ADJ terminal;

a change-over switch which selectively connects one of the other ends of the plurality of fixed resistors or the variable resistors of the resistor group to the other input terminal of the direct-current motor;

a socket to which a battery is attached; and a detection circuit which detects a voltage of a battery, wherein the detection circuit has:

a partial pressure resistor circuit which divides the voltage of the battery to output the divided voltage;

a switching element which is turned ON by an output voltage of the partial pressure resistor circuit; and a notification portion which performs notification when the switching element is turned ON, wherein one of the partial pressure resistors constituting the partial pressure resistor circuit is a variable resistor.

2. The atherectomy device according to claim 1, wherein the resistor group is one having a plurality of potentiometers.

3. The atherectomy device according to claim 2, further comprising:

a setting unit which inputs a pulse into the potentiometers to set a resistance on condition that a current is supplied to the three-terminal regulator.

4. The atherectomy device according to claim 1, further comprising:

a first casing provided with the direct-current motor and having a grip;

a second casing provided with a socket to which a battery which supplies a direct current to the three-terminal regulator is attached, the three-terminal regulator, the resistor group, and the change-over switch; and a cable which electrically connects the output terminal of the three-terminal regulator and the input terminal of the direct-current motor.

5. The atherectomy device according to claim 1, further comprising:

a first casing provided with the direct-current motor, the resistor group, and the change-over switch and having a grip;

a second casing provided with a socket to which a battery is attached; and a cable which electrically connects the battery attached to the socket and the input terminal of the three-terminal regulator.

6. The atherectomy device according to claim 1, further comprising:

a first casing provided with a socket to which a battery which supplies a direct current to the three-terminal regulator is attached, the direct-current motor, the three-terminal regulator, the resistor group, and the change-over switch and having a grip.

7. The atherectomy device according to claim 1, wherein the change-over switch is a rotary switch.

8. An atherectomy device to which a catheter having a tubular body having an opening in a side wall and a cutter which is provided movably in an axial direction in the tubular body is connected, the atherectomy device, comprising:

a bodycasing which has a connection portion to which the catheter is connected and a grip and in which a socket to which a battery is attached is provided;

a substrate in which a three-terminal regulator having an input terminal, an output terminal, and an ADJ terminal is mounted and which is disposed in the bodycasing;

a power switch electrically connected between the battery and an input terminal of the three-terminal regulator;

a direct-current motor which is disposed in the bodycasing, which is connected to the output terminal of the three-terminal regulator, and which rotationally drives a cutter of the catheter; and a partial pressure circuit provided between the output terminal and the ADJ terminal of the three-terminal regulator in the substrate; and wherein the three-terminal regulator is adapted to regulate voltage input to the motor based on the partial pressure circuit connected to the three-terminal regulator;

wherein the partial pressure circuit comprises:

a first resistor coupled at one end to the output terminal of the three-terminal regulator and coupled at an opposite end to the ADJ terminal of the three-terminal regulator; and a second resistor coupled between ground and the ADJ terminal of the three-terminal regulator.

9. The atherectomy device according to claim 8, wherein a light emitting element connected in parallel to the direct-current motor is provided in the body casing.

* * * * *